United States Patent
Baltimore et al.

(10) Patent No.: US 9,090,894 B2
(45) Date of Patent: Jul. 28, 2015

(54) MODULATING IMMUNE SYSTEM DEVELOPMENT AND FUNCTION THROUGH MICRORNA MIR-146

(75) Inventors: David Baltimore, Pasadena, CA (US); Mark Boldin, Pasadena, CA (US); Konstantin Taganov, Pasadena, CA (US)

(73) Assignee: CALIFORNIA INSTITUTE OF TECHNOLOGY, Pasedena, CA (US)

(*) Notice: Subject to any disclaimer, the term of this patent is extended or adjusted under 35 U.S.C. 154(b) by 507 days.

(21) Appl. No.: 12/337,525

(22) Filed: Dec. 17, 2008

(65) Prior Publication Data

US 2009/0203136 A1 Aug. 13, 2009

Related U.S. Application Data

(60) Provisional application No. 61/007,987, filed on Dec. 17, 2007.

(51) Int. Cl.
| | |
|---|---|
| C12N 15/11 | (2006.01) |
| C12Q 1/68 | (2006.01) |
| C12N 15/113 | (2010.01) |
| C07H 21/04 | (2006.01) |

(52) U.S. Cl.
CPC ........ *C12N 15/113* (2013.01); *C12N 2310/111* (2013.01); *C12N 2310/113* (2013.01); *C12N 2310/141* (2013.01); *C12N 2330/10* (2013.01)

(58) Field of Classification Search
None
See application file for complete search history.

(56) References Cited

U.S. PATENT DOCUMENTS

| | | | |
|---|---|---|---|
| 2005/0222067 A1* | 10/2005 | Pfeffer et al. | ............... 514/44 |
| 2005/0261218 A1 | 11/2005 | Esau et al. | |
| 2006/0185027 A1 | 8/2006 | Bartel et al. | |
| 2006/0269519 A1 | 11/2006 | Chen et al. | |
| 2006/0292119 A1 | 12/2006 | Chen et al. | |
| 2007/0232553 A1 | 10/2007 | Baltimore et al. | |

OTHER PUBLICATIONS

Ushijima et al., Characterization of cells of the myeloid-monocytic lineage (ML-1, HL-60, THP-1, U-937) chronically infected with the human immunodeficiency virus-1, 1993, Pathobiology, vol. 61, pp. 145-153.*
Costinean et al., Pre-B cell proliferation and lymphoblastic leukemia/high-grade lymphoma in Emu-miR155 transgenic mice, 2006, PNAS, vol. 103, pp. 7024-7029.*
Wang et al., Identification of a novel lipopolysaccharide-inducible gene with key features of both a kinase anchor proteins and chs1/beige proteins, 2001, The Journal of Immunology, vol. 166, pp. 4586-4595.*
Fujishima et al., Gene expression profiling of human erythroid progenitors by micro-serial analysis of gene expression, 2004, International Journal of Hetatology, vol. 80, pp. 239-245.*
Monticelli et al., MicroRNA profiling of the murine hematopoietic system, 2005, Genome Biology, vol. 6, article R71, pp. 1-15.*
Yamagata et al., A shared gene-expression signature in innate-like lymphocytes, 2006, Immunological Reviews, vol. 210, pp. 52-66.*
Murphy et al., The lineage decisions of helper T cells, 2002, Nature Reviews Immunology, vol. 2, pp. 933-944.*
Huang et al., CD4+ Th1 cells promote CD8+ Tc1 cell survival, memory response, tumor localization and therapy by targeted delivery of interleukin 2 via acquired pMHC I complexes, 2006, Immunology, vol. 120, pp. 148-159.*
Hong et al., Dendritic cell-T cell interactions: CD8alpha alpha expressed on dendritic cells regulates T cell proliferation, 2007, Immunology Letters, vol. 108, pp. 174-178.*
Bartel, "*MicroRNAs: Genomics, Biogenesis, Mechanism, and Function*," Cell, vol. 116, pp. 281-297 (2004).
Fontana et al., "MicroRNAs 17-5p-20a-106a control monocytopoiesis through AML1 targeting and M-CSF receptor upregulation," Nat Cell Biol, vol. 9, pp. 775-787 (2007).
Krützfeldt et al., "*Silencing of microRNAs in vivo with 'antagomirs'*," Nature, vol. 438, pp. 685-689 (2005).
Li et al., "*miR-181a is an Intrinsic Modulator of T Cell Sensitivity and Selection*," Cell, vol. 129, pp. 147-161 (2007).
Taganov et al., "*NF-κB-dependent induction of microRNA miR-146, an inhibitor targeted to signaling proteins of innate immune responses*," Proc Natl Acad Sci USA, vol. 103, pp. 12481-12486 (2006).
International Search Report and Written Opinion dated May 4, 2009 for International Application No. PCT/US2008/087249, Filed Dec. 17, 2008.
International Preliminary Report on Patentability (dated Jul. 1, 2010) in Application No. PCT/NZ2008/087249, filed Dec. 17, 2008.
Chang et al., "Transactivation of miR-34A by p53 Broadly Influences Gene Expression and Promotes Apoptosis", Molecular Cell, 26:745-752 (2007).
Lecellier et al., "A Cellular MicroRNA Mediates Antiviral Defense in Human Cells", Science, 308:557 (2005).
Miller et al., "MicroRNA-221/222 Confers Tamoxifen Resistance in Breast Cancer by Targeting $p27^{Kip1}$ ", Journal of Biological Chemistry, 283(44):29897-29903 (2008).
Ha, "The Role of MicroRNAs in Regulatory T Cells and in the Immune Response", Immune Network, 11(1):11-41 (2011).

* cited by examiner

*Primary Examiner* — Dana Shin
(74) *Attorney, Agent, or Firm* — Knobbe Martens Olson & Bear LLP

(57) ABSTRACT

The present disclosure relates to the finding that microRNA-146 plays a role in modulating the development and function of the immune system. Immune cell development and function can be modulated by delivery of microRNA-146 (miR-146) or antisense miR-146 to target immune cells or precursor cells. For example, in some embodiments, activity and/or proliferation of certain immune cells is regulated by administering miR-146 oligonucleotides or anti-miR-146 oligonucleotides. In other embodiments, pro-inflammatory cytokine expression in immune cells is regulated by administering a miR-146 oligonucleotide or anti-miR-146. In further embodiments, methods of regulating macrophage activity using antisense miR-146 are provided. Additional methods and compositions for regulating immune system function and development using miR-146 are disclosed.

5 Claims, 16 Drawing Sheets

Figure 1
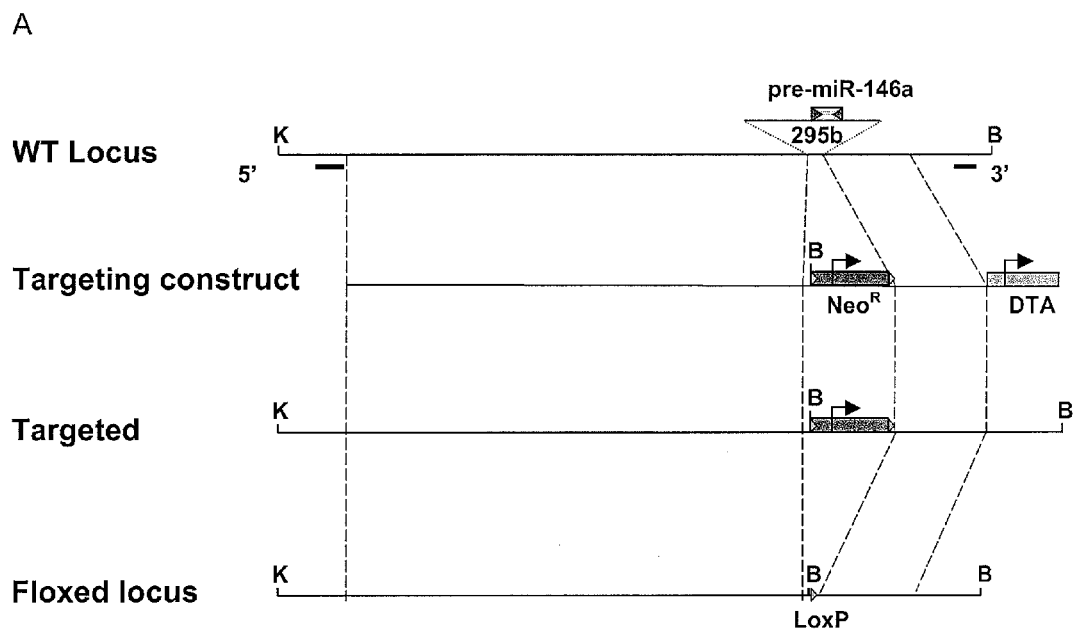
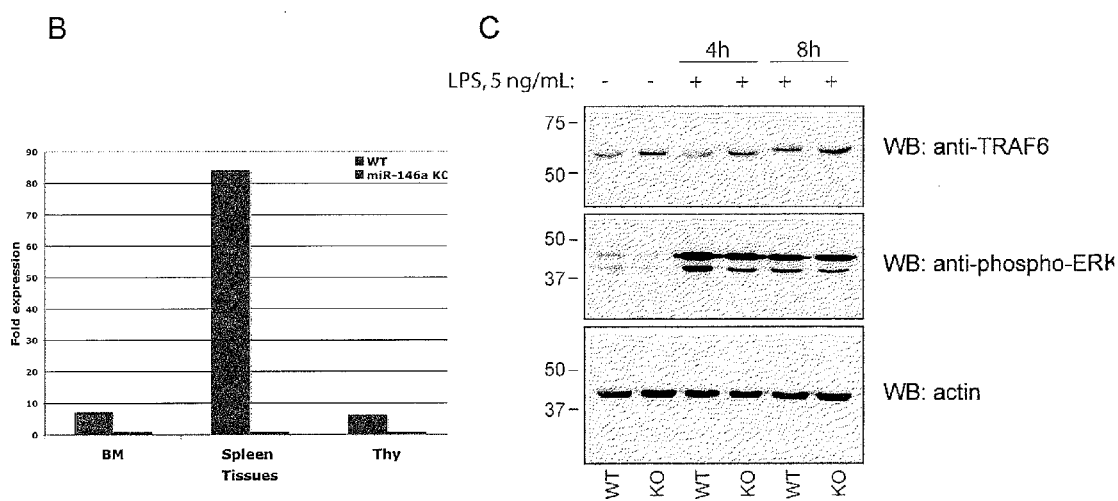

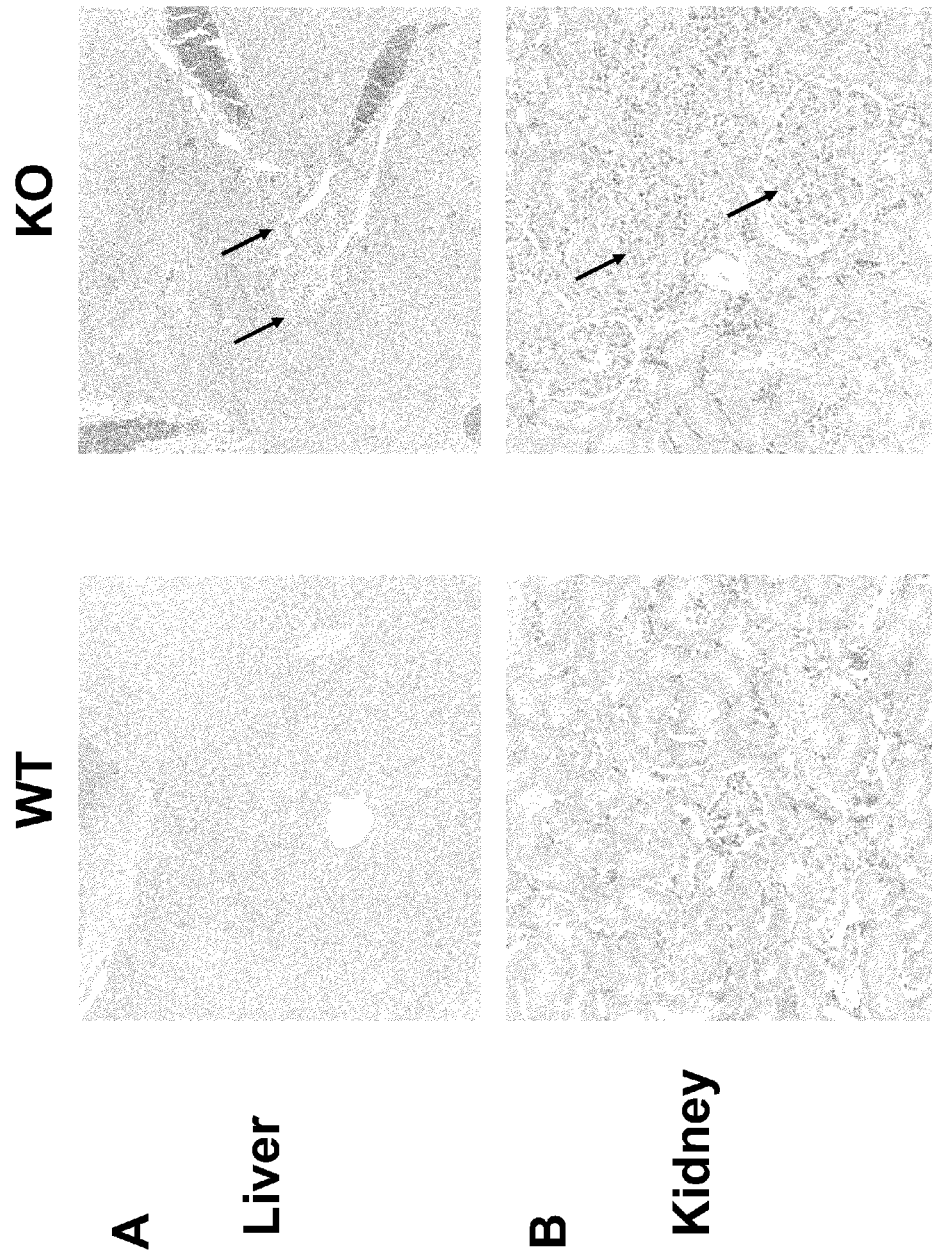

SEQUENCE LISTING

```
<160> NUMBER OF SEQ ID NOS: 14

<210> SEQ ID NO 1
<211> LENGTH: 22
<212> TYPE: RNA
<213> ORGANISM: Human

<400> SEQUENCE: 1
ugagaacuga auuccauggg uu                                              22

<210> SEQ ID NO 2
<211> LENGTH: 99
<212> TYPE: RNA
<213> ORGANISM: Human

<400> SEQUENCE: 2
ccgaugugua uccucagcuu ugagaacuga auuccauggg uugugucagu gucagaccuc     60
ugaaauucag uucuucagcu gggauaucuc ugucaucgu                            99

<210> SEQ ID NO 3
<211> LENGTH: 22
<212> TYPE: RNA
<213> ORGANISM: Human

<400> SEQUENCE: 3
ugagaacuga auuccauagg cu                                              22

<210> SEQ ID NO 4
<211> LENGTH: 73
<212> TYPE: RNA
<213> ORGANISM: Human

<400> SEQUENCE: 4
ccuggcacug agaacugaau uccauaggcu gugagcucua gcaaugcccu guggacucag     60
uucuggugcc cgg                                                        73

<210> SEQ ID NO 5
<211> LENGTH: 22
<212> TYPE: DNA
<213> ORGANISM: Human

<400> SEQUENCE: 5
tgagaactga attccatggg tt                                              22
```

```
<210> SEQ ID NO 6
<211> LENGTH: 99
<212> TYPE: DNA
<213> ORGANISM: Human

<400> SEQUENCE: 6
ccgatgtgta tcctcagctt tgagaactga attccatggg ttgtgtcagt gtcagacctc    60
tgaaattcag ttcttcagct gggatatctc tgtcatcgt                           99

<210> SEQ ID NO 7
<211> LENGTH: 22
<212> TYPE: DNA
<213> ORGANISM: Human

<400> SEQUENCE: 7
tgagaactga attccatagg ct                                             22

<210> SEQ ID NO 8
<211> LENGTH: 73
<212> TYPE: DNA
<213> ORGANISM: Human

<400> SEQUENCE: 8
cctggcactg agaactgaat tccataggct gtgagctcta gcaatgccct gtggactcag    60
ttctggtgcc cgg                                                       73

<210> SEQ ID NO 9
<211> LENGTH: 22
<212> TYPE: RNA
<213> ORGANISM: Artificial Sequence
<220> FEATURE:
<223> OTHER INFORMATION: Anti-sense miR-146a

<400> SEQUENCE: 9
aacccaugga auucaguucu ca                                             22

<210> SEQ ID NO 10
<211> LENGTH: 22
<212> TYPE: RNA
<213> ORGANISM: Artificial Sequence
<220> FEATURE:
<223> OTHER INFORMATION: Anti-sense miR-146b

<400> SEQUENCE: 10
agccuaugga auucaguucu ca                                             22

<210> SEQ ID NO 11
<211> LENGTH: 22
<212> TYPE: DNA
<213> ORGANISM: Artificial Sequence
<220> FEATURE:
<223> OTHER INFORMATION: Anti-sense miR-146a

<400> SEQUENCE: 11
aacccatgga attcagttct ca                                             22

<210> SEQ ID NO 12
<211> LENGTH: 22
<212> TYPE: DNA
<213> ORGANISM: Artificial Sequence
<220> FEATURE:
<223> OTHER INFORMATION: Anti-sense miR-146b

<400> SEQUENCE: 12
```
agcctatgga attcagttct ca    22

<210> SEQ ID NO 13
<211> LENGTH: 2337
<212> TYPE: DNA
<213> ORGANISM: Human

<400> SEQUENCE: 13

| | | | | | |
|---|---|---|---|---|---|
| tctccaagac | gcttgaccgc | tcttcctttc | ctggatggca | ccagcagggc | cgattggagt | 60 |
| ggtaaaccct | gggccggaag | gcatgccaaa | gggtggacag | gatggacagg | agacagtagc | 120 |
| acaacgagga | ggggagaac | agtggctgaa | ttggaaatga | taaataaaa | tgaaatttta | 180 |
| ggagctcgct | ggctgggaca | ggcctggact | gcaaggaggg | gtctttgcac | catctctgaa | 240 |
| aagccgatgt | gtatcctcag | ctttgagaac | tgaattccat | gggttgtgtc | agtgtcagac | 300 |
| ctgtgaaatt | cagttcttca | gctgggatat | ctctgtcatc | gtgggcttga | ggacctggag | 360 |
| agagtagatc | ctgaagaact | ttttcagtct | gctgaagagc | ttggaagact | ggagacagaa | 420 |
| ggcagagtct | caggctctga | aggtataagg | agtgtgagtt | cctgtgagaa | acactcattt | 480 |
| gattgtgaaa | agacttgaat | tctatgctaa | gcagggttcc | aagtagctaa | atgaatgatc | 540 |
| tcagcaagtc | tctcttgctg | ctgctgctac | tcgtttacat | ttattgatta | cttacgatga | 600 |
| ttcaggtact | gttgtaagtg | ctttacatgc | tgttatacga | gactcttggg | agaaatcact | 660 |
| ttaatgaagc | ttgagacaca | tggcattgcc | atgcaatgat | ttttcccccc | tcttcacggg | 720 |
| atcagaggga | actaatagaa | tgtgacaatg | attcttttagc | agggactgct | gaggcttctg | 780 |
| gttccttttt | aagatctgca | gtgaaagaag | atgagaaaca | tggatatgcc | cttcttttgg | 840 |
| tcccctctt | cctttatttg | atctctactt | ccttctataa | atatattagg | gctacattgt | 900 |
| cccttgtat | ttcaaacaag | gcaaaagag | gttgtaatta | cactttactg | caatcctcag | 960 |
| tttctccagg | gaacaggaat | gcaaaggctt | tgaaggcctc | tctatttgct | gacatggtca | 1020 |
| gctgggtgcc | atgggccaag | tccttctgtt | gccctcctct | gtcaccaagt | aagctaggtc | 1080 |
| ctttctgagg | ctcaggtttg | ctgtgatgat | gatcactttt | aggcagaagg | ttagaggcct | 1140 |
| catgagtgct | atatggactt | tattaggctt | tagatttgat | ggggaataag | ggatgtgatt | 1200 |
| tgtcttttgg | gaactcatct | ttgattcatc | attgtctctt | ggtatcttgg | aatttccatg | 1260 |
| tcattacagt | ctacagaatg | aaagagtaac | ctgtcccaga | ggagaggcag | gtgaaagact | 1320 |
| ccacagcatg | ctcattctca | ttctgtcttc | tcagtgacac | cgaggtttac | tgagtgccca | 1380 |
| ctatgtgcca | agcactgtgc | tcagggcttt | cttttgtatgc | atgatctcag | tgaatctcac | 1440 |
| caagcctcat | ctggaaaacg | gggacaaatt | aacaacagga | tggcaaattg | aaaaacacgt | 1500 |
| aaccatgttc | tacagatgga | aaggggtgct | tggttattat | gaaggccccc | tcgcaagcgt | 1560 |
| gtgggacatg | ggtgtgttct | ctgggttgta | ctgatcagat | caaggacctc | ccccacccctt | 1620 |
| ctcacactct | gcccacttcc | gcccctttgct | tatcagaccc | ttagccagtg | actcattcca | 1680 |
| gaaccagaac | cttggtgaaa | tctcaaccga | caccagagat | cggtgtcttc | agtcctagac | 1740 |
| tgatggagaa | aatccagaat | atatactaga | agctccaaat | gctctgggtt | tcagctcctc | 1800 |
| tgtgctgtgg | acactgactt | tggctcagaa | ctccgatttta | gtacaaaagg | ctcatttta | 1860 |
| tttcaggggc | actcttccta | aagcaaacct | aataaatgaa | atatggaatt | cacagataca | 1920 |
| cacacacatt | aaaaaattaa | cctagtgtat | ctgtgaggag | taggcagaaa | ttcactgtat | 1980 |
| aaaagaatgc | ttcatttcat | agagaatttg | tgttaagatt | ccattagata | gtacatttct | 2040 |

```
caaagattttt tgaggttgta tttgctttac caaaacttgg tttatgtaag tggaaaaagc    2100
atgttgcaaa ataacttggt gtctatgatt cagtttatgt aaaataataa atgtatgtag    2160
gaatacgtgt gttgaaagat gtacatcaat ttgctaacaa tggttatctc tgacgtggtg    2220
ggatttgaga tgtgttttc tttttggttg tattttctc tattgtttga cttaacacag      2280
aacatgcttg gttacaacaa taaagttatt gaagacaaaa aaaaaaaaa aaaaaaa        2337

<210> SEQ ID NO 14
<211> LENGTH: 6
<212> TYPE: RNA
<213> ORGANISM: Human

<400> SEQUENCE: 14 gagaac                                                                     6
```

MODULATING IMMUNE SYSTEM DEVELOPMENT AND FUNCTION THROUGH MICRORNA MIR-146

CROSS-REFERENCE TO RELATED APPLICATIONS

The present application claims priority under 35 U.S.C. §119(e) to U.S. Provisional Application No. 61/007,987, filed on Dec. 17, 2007, which is herein expressly incorporated by reference.

STATEMENT REGARDING FEDERALLY SPONSORED R&D

The U.S. Government has certain rights in this invention pursuant to Grant No. GM039458 awarded by National Institutes of Health.

REFERENCE TO SEQUENCE LISTING

The present application is being filed along with a Sequence Listing in electronic format. The Sequence Listing is provided as a file entitled CALTE_045A.TXT, created Dec. 17, 2008, which is 5.2 KB in size. The information in the electronic format of the Sequence Listing is incorporated herein by reference in its entirety.

BACKGROUND OF THE INVENTION

1. Field of the Invention

The present application relates to modulating the activity of the immune system using microRNA. More particularly the application relates to modulating immune system development and function through miR-146.

2. Description of the Related Art

Historically, the innate and adaptive arms of the immune response have been represented as two separate systems with distinct properties. However, there are several types of immune cells whose phenotypic features place them at the border of the innate and adaptive systems and provide a bridge between the two. This list includes B1 B cell, marginal zone (MZ) B cells, natural killer T (NKT) cells, γδ T cells and intestinal epithelial lymphocytes (IEL) expressing CD8αα. These lineages are shown to be essential for several aspects of immunity because their dysfunction or deficiency has been shown to lead to the development of autoimmune disease and cancers. Each of the above-mentioned cell types is characterized by a unique set of anatomical location, self-renewing capacity, surface phenotype and ligands.

For instance, B-1 cells are known to function as innate-like immunity effectors and are the key players in the early humoral response against bacteria, viruses, and certain parasites. Montecino-Rodriguez, Trends Immunol 27, 428-433. B1 cells are located mainly in the peritoneal and pleural cavities, and express high levels of surface IgM and low levels of IgD, CD23, and B220. They are thought to be the primary antibody producers in response to T cell-independent type 2 antigens, such as capsular polysaccharides on bacteria. Importantly, natural antibodies produced by B1 cells also bind to self-antigens, and this property could explain why B1 cells are often associated with autoimmune diseases in mice and humans.

Another example of B cells that play an important role in T cell-independent antibody response is MZ B cells. Viau and Zouali, Clin Immunol 114, 17-26. They are located at the junction of white and red pulp and have a surface phenotype distinct from other spleen B cells. MZ B cells respond vigorously to blood-borne infections, and play a role in host survival of infection by encapsulated bacteria.

A group of unconventional T cells that possess properties of both the innate and adaptive systems are the IEL cells. This subtype exclusively expresses CD8αα; however, they do not express either of the well-defined CD4 or CD8αβ TCR coreceptors, or several molecules found on most other T lymphocytes, such as CD2, CD28, and CD 90.

MicroRNA (miRNA) represent a newly discovered class of endogenous ~22-nt RNAs encoded by biological species. Owing to their ability to post-transcriptionally regulate expression of nearly any target gene, miRNA have been implicated in a variety of processes in plants and animals, and have been shown to be involved in development, apoptosis, signal transduction, fat metabolism, insulin secretion, viral infection, and potentially many other processes. Bartel, Cell 116, 281-297. A growing body of evidence suggests that miRNAs play an important role in all aspects of immune system development and function from driving differentiation of certain cell lineages to fine-tuning of immune response to antigen. Fontana, Nat Cell Biol 9, 775-787; Li, Cell 129, 147-161.

Inflammation is a highly complex defense reaction of the host in response to an invading pathogen or injury, which when not resolved swiftly can result in quite severe pathological consequences. The importance of timely resolution of inflammatory reaction is underscored by the number of diseases where a failure to terminate inflammatory process is the main driving force, like rheumatoid arthritis, septic shock, inflammatory bowel disease and multiple sclerosis. In addition, there is mounting evidence that sustained inflammation is linked to various human cancers.

MicroRNAs have been shown to be involved in regulation of the innate immune response, and miRNAs that play a role in the mammalian response to microbial infection have been identified. Taganov, Proc Natl Acad Sci USA 103, 12481-12486.

SUMMARY OF THE INVENTION

Immune system development and function can be modulated by means of microRNA expression or targeted delivery of said microRNA to the immune system, and by preventing normal microRNA activity, such as by knocking out the genes that encode said MicroRNA or by administering antisense sequences of said microRNA.

Methods for regulating development and function of immune cells are provided in accordance with one aspect of the present invention. In some embodiments, a miR-146 oligonucleotide or antisense miR-146 oligonucleotide are administered to a target cell, such as an immune precursor cell. Proliferation of one or more of B1 B cells, B2 B cells, Marginal Zone B cells, CD8αα+ T cells, Natural Killer cells or CD8+ T cells can then be measured to identify an effect on immune cells. In some embodiments, the miR-146 oligonucleotide or antisense miR-146 oligonucleotide are administered to bone marrow in a mammal.

In some embodiments, proliferation and function of immune cells, such as B1 B cells, B2 B cells, Marginal Zone B cells, CD8αα+ T cells, Natural Killer cells and CD8+ T cells can be regulated using miRNA-146 or antisense miRNA-146. In some embodiments, the methods comprise administering a microRNA-146a (miR-146a) or microRNA-146b (miR-146b) oligonucleotide to target cells. In other embodiments, the methods comprise administering a miR-146a or miR-146b expression vector to target cells such that a miRNA-146 is expressed in target cells. In other embodiments, the methods comprise administering antisense miRNA-146 or other molecules that interfere with miR-146 expression or activity to target cells expressing miRNA-146.

In some embodiments methods of increasing proliferation and/or activity of immune cells, such as B1 B cells, Marginal Zone B cells and Natural Killer cells and CD8+ T cells, are provided. In some embodiments, the methods comprise administering a miRNA-146 oligonucleotide to a target cell or target tissue, such as bone marrow. In other embodiments, the methods comprise administering a miRNA-146 expression vector to target cells or a target tissue and expressing a miRNA-146 in the target. In some embodiments, total numbers of one or more of B1 B cells, Marginal Zone B cells and Natural Killer cells and CD8+ T cells can be increased in a host by these methods.

In other embodiments, methods of decreasing proliferation and/or activity of immune cells such as B1 B cells, Marginal Zone B cells and Natural Killer cells and CD8+ T cells are provided. In some embodiments, the methods comprise administering antisense miRNA-146 oligonucleotides to target cells or a target tissue, such as bone marrow. In other embodiments, the methods comprise administering an antisense miRNA-146 expression vector to target cells or a target tissue such that antisense miRNA-146 is expressed in the target. In some embodiments, total numbers of one or more of B1 B cells, Marginal Zone B cells and Natural Killer cells and CD8+ T cells can be decreased in a host by these methods.

In other embodiments, proliferation and/or activity of immune cells such as B2 B cells and CD8αα+ T cells can be upregulated. In some embodiments, the methods comprise administering an antisense miRNA-146 oligonucleotide to target cells or a target tissue, such as bone marrow. In other embodiments, the methods comprise administering an antisense miRNA-146 expression vector to a target tissue such that antisense miRNA-146 is expressed in the target tissue. In some embodiments, total numbers of B2 B cells and/or CD8αα+ T cells can be increased in a host by these methods.

In other embodiments, proliferation and/or activity of B2 B cells and CD8αα+ T cells can be downregulated. In some embodiments, the methods comprise administering a miRNA-146 oligonucleotide to target cells or a target tissue, such as bone marrow. In other embodiments, the methods comprise administering a miRNA-146 expression vector to a target tissue and expressing a miRNA-146 in the target tissue. In some embodiments, total numbers of B2 B cells and/or CD8αα+ T cells can be decreased in a host by these methods.

Methods for modulating T cell activation are provided in accordance with yet another aspect of the present invention. In some embodiments, the T cell activation is downregulated by administering a miR-146 oligonucleotide to the target T cells. In other embodiments, the methods comprise administering a miR-146 expression vector to target T cells and expressing a miRNA-146 in the target cells. In some embodiments, diseases or disorders related to T cell activation, such as inflammatory bowel disease, rheumatoid arthritis, lupus and multiple sclerosis, can be treated by administering a miR-146 oligonucleotide or expression vector to immune cells in a patient in need of treatment.

Methods for downregulating production of certain pro-inflammatory cytokines by immune cells is provided in accordance with another aspect of the present invention. In some embodiments the production of pro-inflammatory cytokines by immune cells, such as macrophages or T cells, is down-regulated by administering a miR-146 oligonucleotide to target immune cells, or by expressing a miR-146 oligonucleotide in target cells. In particular embodiments, macrophage function can be regulated by administering miR-146 or anti-sense miR-146 to macrophages or macrophage precursor cells.

In some embodiments the production of TNFα and/or IL-6 is downregulated by administering a microRNA-146 (miR-146) oligonucleotide to target immune cells, such as macrophages or T cells. In other embodiments, a miRNA-146 is expressed in target immune cells by administering a miR-146 expression vector to the target cells. If desired, levels of pro-inflammatory cytokines TNFα and/or IL-6 can be upregulated by administering anti-sense miR-146 to target immune cells or expressing antisense-miR146 in target cells.

Methods for regulating activation of certain kinases in immune cells are also provided. More specifically, in some embodiments the activation of NF-kB and/or JNK1 can be downregulated by administering a miRNA-146 oligonucleotide to target immune cells. In other embodiments, a miRNA-146 expression vector can be administered to a target cell such that a miRNA-146 is expressed in the target immune cell. In other embodiments the activation of ERK can be downregulated in immune cells. In some embodiments, the methods comprise administering miRNA-146 oligonucleotide to a target immune cell. In other embodiments, the methods comprise administering an antisense miRNA-146 expression vector to a target cell and expressing an antisense miRNA-146 in the target cell.

BRIEF DESCRIPTION OF THE DRAWINGS

FIG. 1 shows generation of miR-146 knock out (KO) mice. (A). A 295 bp pre-miR-146a encoding region was replaced by a PGK-Neo cassette flanked by loxP sites, and in the next step was loxed out with the help of Cre-deleter mice. (B). Detection of expression levels of mature miR-146a in wild type and mutant mice by qRT-PCR analysis of spleen, lymph nodes, and thymus. (C). Western blot analysis of cell lysates from LPS stimulated BMDMs derived from wild type (WT) and KO animals.

Figure 2:
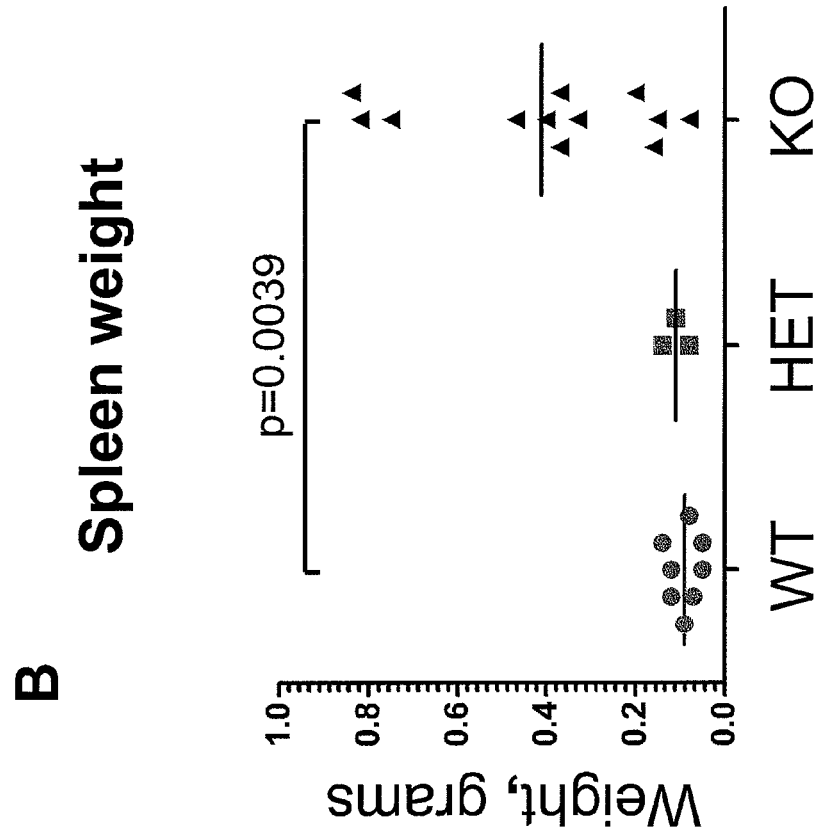
FIG. 2 shows miR-146a KO mice develop autoimmune-like disease that is characterized by splenomegaly and lymphoadenopathy. (A). Representative examples of large spleen and big lymph nodes observed in KO animals (B). Increase in spleen weight in the KO animals.

DETAILED DESCRIPTION OF CERTAIN EMBODIMENTS miR-146 can be used to modulate immune system development and function. As a result, it can be used, for example, as a therapeutic agent to treat disease states, including those characterized by activation, particularly excessive activation of the innate immune system. Such disease states include, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis, lupus, multiple sclerosis and Crohn's disease.

When miR-146a or miRNA-146b is delivered into cells of the innate immune system, among other things it dampens the production of pro-inflammatory cytokines like TNF and IL-6. Such delivery can be achieved in a variety of ways using methods well known in the art, for example, by modification of an oligonucleotide encoding a miR-146, such as a mature miR-146a or miR-146b, with cholesterol to help it easily penetrate the cell membrane or by expressing the miRNA in the cells using an appropriate expression vector. See, for example, Krutzfeldt, J. et al., *Nature* 438, 685-9 (2005), herein expressly incorporated by reference. Delivery of molecules that inhibit miR-146 activity, such as antisense molecules, can be used to upregulate activity of the immune system where appropriate. These and other embodiments are discussed in more detail below.

Human miR-146a is located in the second exon of LOC285628 gene on the human chromosome 5. LOC285628 consists of two exons separated by a long ~16 kb long intron and is most probably a non-coding RNA gene, since it does not contain a long, continuous open reading frame. MiR-146b is located on human chromosome 10.

In some embodiments, immune cell function, proliferation and numbers can be modulated by modulating levels of miR-146 in target cells and tissues. Upregulation of miRNA-146 in target organs, tissues and/or cells can be accomplished by, for example, administering to the target either synthetic miR-146, such as a miR-146 oligonucleotide, or expression vectors that express miRNA-146. Downregulation of miRNA-146 in target cells, organs or tissues can be accomplished by, for example, by administering to the target an anti-miR-146, such as by administering synthetic antisense miRNA-146, expression vectors that express antisense miRNA-146 or administering one or more other molecules that interfere with miR-146 expression or activity.

For example, in some embodiments B1 B cell activity and/or proliferation can be upregulated by administering miRNA-146 to target immune cells or precursor cells. CD8+ CD3+ conventional T cell activity and/or proliferation can be upregulated by administering miRNA-146. B2 B cell activity and/or proliferation can be downregulated by administering miRNA-146. CD8αα+ T cell activity and/or proliferation can be downregulated by administering miRNA-146.

CD-11b+ cell activity and/or proliferation can be upregulated by administering anti-miR-146 to target immune cells or precursor cells. B1 B cell activity and/or proliferation can be downregulated by administering antisense miR-146. CD8+ T cell activity and/or proliferation can be downregulated by administering antisense miR-146. B2 B cell activity and/or proliferation can be upregulated by administering antisense miRNA-146. CD8αα+ T cell activity and/or proliferation can be upregulated by administering antisense miRNA-146.

In some embodiments, vaccination, such as cancer vaccination can be improved by modulating miR146a levels in an animal. For example, anti-miR-146 can be delivered to the target animal to be vaccinated, increasing the activity and/or number of CD8αα+ T cells. Because CDαα+ T cells are considered to be precursors of memory T cells, increased activity and/or numbers of CDαα+ T cells increases the desired immune response to a vaccine. The vaccine can be administered before, concurrently with or after the ani-miR-146.

In some embodiments, production of pro-inflammatory cytokines, such as TNFα and IL-6 levels, by immune cells can be downregulated by modulating levels or activity of miRNA-146 in target cells. TNFα and IL-6 production can be downregulated by administering miRNA-146 to the target cells.

In some embodiments, T cell activation, for example as indicated by the increased expression levels of surface markers, such as CD25, CD69 and CD44, can be reduced by modulating levels of miRNA-146 target cells. In some embodiments, T cell activation can be downregulated by administering miRNA-146 to target cells. Because T cell activation is related to some diseases or disorders, such as inflammatory bowel disease, rheumatoid arthritis, lupus and multiple sclerosis, administration of miRNA-146 to a patient in need of treatment can be used to treat such disorders.

DEFINITIONS

Unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). For purposes of the present invention, the following terms are defined below.

When used herein the terms "miR," "mir" and "miRNA" are used to refer to microRNA, a class of small RNA molecules that are capable of modulating RNA translation (see, Zeng and Cullen, RNA, 9(1):112-123, 2003; Kidner and Martienssen Trends Genet, 19(1):13-6, 2003; Dennis C, Nature, 420(6917):732, 2002; Couzin J, Science 298(5602):2296-7, 2002, each of which is incorporated by reference herein).

"MiRNA-146," "miR-146," "miR-146a/b" and "miRNA-146a/b" are used interchangeably and, unless otherwise indicated, refer to microRNA-146a and/or microRNA-146b, including miR-146a, pri-miR-146a, pre-miR-146a, mature miR-146a, miR-146b, pre-miR-146b, mature miR-146b, miRNA-146 seed sequence, sequences comprising a miRNA-146 seed sequence, and variants thereof.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, such as constitutive or inducible promoters.

"MiRNA nucleic acid" is defined as RNA or DNA that encodes a miR as defined above, or is complementary to a nucleic acid sequence encoding a miR, or hybridizes to such RNA or DNA and remains stably bound to it under appropriate stringency conditions. Specifically included are genomic DNA, cDNA, mRNA, miRNA and antisense molecules, pri-miRNA, pre-miRNA, mature miRNA, miRNA seed sequence, as well as nucleic acids based on alternative backbones or including alternative bases. MiRNA nucleic acids can be derived from natural sources or synthesized.

"MicroRNA seed sequence," "miRNA seed sequence," "seed region" and "seed portion" are used to refer to nucleotides 2-7 or 2-8 of the mature miRNA sequence. The miRNA seed sequence is typically located at the 5' end of the miRNA. A miRNA-146 seed sequence is provided in SEQ ID NO: 14.

The term "operably linked" is used to describe the connection between regulatory elements and a gene or its coding region. That is, gene expression is typically placed under the control of certain regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element.

The term "mammal" is defined as an individual belonging to the class Mammalia and includes, without limitation, humans, domestic and farm animals, and zoo, sports, or pet animals, such as sheep, dogs, horses, cats or cows. Preferably, the mammal herein is human. However, in some embodiments the mammal is not a human.

As used herein, "treatment" is a clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. "Treatments" refer to one or both of therapeutic treatment and prophylactic or preventative measures. Those in need of treatment include those already affected by a disease or disorder or undesired physiological condition as well as those in which the disease or disorder or undesired physiological condition is to be prevented.

The term "effective amount" refers to an amount sufficient to effect beneficial or desirable biological and/or clinical results.

"Pharmaceutically acceptable" carriers, excipients, or stabilizers are ones which are nontoxic to the cell or mammal being exposed thereto at the dosages and concentrations employed or that have an acceptable level of toxicity as determined by the skilled practitioner. Often the physiologically acceptable carrier is an aqueous pH buffered solution. The physiologically acceptable carrier may also comprise one or more of the following: antioxidants, such as ascorbic acid, low molecular weight (less than about 10 residues) polypeptides, proteins, such as serum albumin, gelatin, immunoglobulins, hydrophilic polymers such as polyvinylpyrrolidone, amino acids, carbohydrates such as glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™.

MiR-146 Nucleic Acid Molecules

Nucleic acid molecules that encode miR-146 are used in various embodiments of the present invention. miR-146 sequences for mature miR-146a, pre-miR-146a, mature miR-146b and pre-miR-146b are provided in SEQ ID NOs: 1, 2, 3 and 4, respectively and are used in some embodiments. cDNAs encoding mature miR-146a, pre-miR-146a, mature miR-146b and pre-miR-146b, are provided in SEQ ID NOs: 5, 6, 7 and 8, respectively. Nucleic acid molecules encoding pri-miR-146a and pri-miR-146b sequences can also be used in accordance with some embodiments. A miRNA sequence may comprise from about 6 to about 99 or more nucleotides. In some embodiments, a miRNA sequence comprises about the first 6 to about the first 22 nucleotides of a pre-miRNA-146. Isolated or purified polynucleotides having at least 6 nucleotides (i.e., a hybridizable portion) of a miR-146 coding sequence or its complement are used in some embodiments. In other embodiments, miR-146 polynucleotides preferably comprise at least 22 (continuous) nucleotides, or a full-length miR-146 coding sequence.

In some embodiments, nucleic acids are used that are capable of blocking the activity of a miRNA (anti-miRNA-146 or anti-miR-146). Such nucleic acids include, for example, antisense miR-146. In preferred embodiments, the anti-miR is an antisense miR-16 nucleic acid comprising a total of about 5 to about 100 or more, more preferably about 10 to about 60 nucleotides, and has a sequence that is preferably complementary to at least the seed region of miR-146. In particularly preferred embodiments, an anti-miRNA may comprise a total of at least about 5, to about 26 nucleotides. In some embodiments, the sequence of the anti-miRNA can comprise at least 5 nucleotides that are substantially complementary to the 5' region of a miR-146, at least 5 nucleotides that are substantially complementary to the 3' region of a miR-146, at least 4-7 nucleotides that are substantially complementary to a miR-146 seed sequence, or at least 5-12 nucleotide that are substantially complementary to the flanking regions of a miR-146 seed sequence.

It is not intended that the methods of the present invention be limited by the source of the miR-146 or anti-miR-146. Human and mouse synthetic miR-146a and miR-146b are commercially available, as are inhibitors thereof. For example, both miRNA precursors and miRNA inhibitors for miR-146a and miR-146b can be purchased from Ambion®. It has been shown that antisense miRNAs can specifically silence target miRNA in tissue. Krutzfeldt, J. et al., Nature 438, 685-9 (2005).

In some embodiments, an anti-miR-146 comprises the complement of a sequence of a miRNA referred to in SEQ ID NOs: 1-4. In other embodiments an anti-miR-146 comprises the complement of the seed sequence of SEQ ID NO: 14 or is able to hybridize under stringent conditions to the seed sequence of SEQ ID NO: 14. Preferred molecules are those that are able to hybridize under stringent conditions to the complement of a cDNA encoding a mature miR-146, for example SEQ ID NO: 1 or SEQ ID NO: 3. Particular antisense sequences for miR-146a and miR-146b are provided in SEQ ID NOs: 9 and 10.

The miR-146 can be from a human or non-human mammal, derived from any recombinant source, synthesized in vitro or by chemical synthesis. The nucleotide may be DNA or RNA and may exist in a double-stranded, single-stranded or partially double-stranded form, depending on the particular context. miR-146 and anti-miR-146 nucleic acids may be prepared by any conventional means typically used to prepare nucleic acids in large quantity. For example, nucleic acids may be chemically synthesized using commercially available reagents and synthesizers by methods that are well-known in the art for example, the phosphotriester method of Matteucci, et al., (J. Am. Chem. Soc. 103:3185-3191, 1981) and/or using automated synthesis methods. (See, e.g., Gait, 1985, Oligonucleotide Synthesis: A Practical Approach, IRL Press, Oxford, England). In addition, larger DNA or RNA segments can readily be prepared by well known methods, such as synthesis of a group of oligonucleotides that define various modular segments, followed by ligation of oligonucleotides to build the complete segment. The scope of the current invention is not limited to naturally occurring miR-146 sequences; mutants and variants of miR-146 sequences are also covered by the scope of the current invention.

Nucleotide sequences that encode a mutant of a miR-146 that is a miR-146 with one or more substitutions, additions and/or deletions, and fragments of miR-146 as well as truncated versions of miR-146 maybe also be useful in the methods of the present invention.

To increase stability and/or optimize delivery of the sense or antisense oligonucleotides, modified nucleotides or backbone modifications can be utilized. For example, modified nucleotides may include: linked nuclear acid (LNA), 2'-O-Me nucleotides, 2'-O-methoxyethyl, and 2' fluoro. Backbone modifications include, for example, phosphorothioate and phosphate.

In some embodiments, a miR-146 or anti-miR-146 oligonucleotide is modified with cholesterol to enhance delivery to target cells. The cholesterol can be linked, for example, through a hydroxyprolinol linkage on the 3' end of the miRNA.

Nucleic acid molecules encoding miR-146 and anti-miR-146 are used in some embodiments of the present invention, for example to modulate function, activity and/or proliferation of immune cells.

MiR-146 Expression Vectors

Expression vectors that contain a miR-146 or anti-miR-146 coding sequence are also useful in the present invention for delivery of a miR-146 or anti-miR146 to target cells. Thus the present invention also contemplates expression vectors that contain a miR-146 sequence and/or anti-miR-146 sequence, optionally associated with a regulatory element that directs the expression of the coding sequence in a target cell. MiR-146 sequences are described in detail in the previous section. The choice of vector and/or expression control sequences to which the encoding sequence is operably linked depends directly, as is well known in the art, on the functional properties desired, e.g., miRNA transcription, and the host cell to be transformed.

A vector contemplated by the present invention is preferably capable of directing replication in an appropriate host and of expression of a miR-146 or anti-miR-146 in a target cell. Vectors that can be used are well known in the art and include, but are not limited to, pUC8, pUC9, pBR322 and pBR329 available from BioRad Laboratories, (Richmond, Calif.), pPL and pKK223 available from Pharmacia (Piscataway, N.J.) for use in prokaryotic cells, and pSVL and pKSV-10 (Pharmacia), pBPV-1/pML2d (International Biotechnologies, Inc.), pCDNA and pTDT1 (ATCC, #31255), for use in eukaryotic cells, as well as eukaryotic viral vectors such as adenoviral or retroviral vectors.

Vectors may include a selection gene whose expression confers a detectable marker such as a drug resistance. Typical selection genes encode proteins that confer resistance to antibiotics or other toxins, e.g., ampicillin, neomycin, methotrexate, or tetracycline, complement auxotrophic deficiencies, or supply critical nutrients withheld from the media. Such selection systems are well known in the art. The selectable marker can optionally be present on a separate plasmid and introduced by co-transfection.

Expression control elements that are used for regulating the expression of an operably linked coding sequence are known in the art and include, but are not limited to, inducible promoters, constitutive promoters, enhancers, and other regulatory elements. In some embodiments an inducible promoter is used that is readily controlled, such as being responsive to a nutrient in the target cell's medium. In some embodiments, the promoter is the U6 promoter or CMV promoter.

Other methods, vectors, and target cells suitable for adaptation to the expression of miR-146 in target cells are well known in the art and are readily adapted to the specific circumstances.

Delivery of Oligonucleotides and Expression Vectors to a Target Cell or Tissue

In some embodiments, a miR-146 or anti-miR-146 oligonucleotide is delivered to a target cell. In other embodiments, an expression vector encoding a miR-146 or anti-miR-146 is delivered to a target cell where the miR-146 or anti-miR-146 is expressed. Methods for delivery of oligonucleotides and expression vectors to target cells are well known in the art and exemplary methods are described briefly below. Target cells can be, for example, any immune cell, such as immune cells involved in innate immunity, or precursors of immune cells. Target cells may be present in a host, such as in a mammal, or may be in culture outside of a host. Delivery of miR-146 or anti-miR-146 to target cells in vivo, ex vivo and in vitro is contemplated, depending on the particular circumstances.

In some embodiments, a miR-146 or anti-miR-146 oligonucleotide is delivered to a target organ or tissue. Target organs and tissues may include locations where hematopoietic and/or immune cells or precursors of such cells are known to be located and may include, for example and without limitation, the peritoneal cavity, spleen, lymph nodes, including mesenteric lymph nodes and peripheral lymph nodes, thymus, and bone marrow. In some embodiments, immune cell development, function, proliferation and/or activity is modulated by delivering miR-146 or anti miR-146 to bone marrow. In other embodiments, the numbers and/or activity of B1 B cells can be modulated by administering a miRNA-146 or anti-miR-146 oligonucleotide to B1 B cells in peritoneal cavity or to B1 B precursor cells in the bone marrow. The numbers and/or activity of B2 B cells can be modulated by administering a miRNA-146 or anti-miR-146 oligonucleotide to the bone marrow or to B2 B cells or B2 B precursor cells in the bone marrow or elsewhere. The activity and/or numbers of CD8+CD3+ conventional T cells can be modulated by administering a miRNA-146 or anti-miR-146 oligonucleotide to these cells, for example in the spleen, or to precursor cells in the elsewhere, such as in the bone marrow. The numbers and/or activity of CD8αα+ T cells can be modulated by administering a miRNA-146 or anti-miR-146 oligonucleotide to these cells, for example, in mesenteric lymph nodes, or to precursor cells in the bone marrow or elsewhere. The numbers and/or activity of CD-11b+ cells, for example in the spleen, can be modulated by administering a miRNA-146 or antisense miRNA-146 to these cells or precursor cells in the spleen or elsewhere. In some embodiments, immune cell function and/or development is modulated by delivering miR-146 or anti-miR-146 to the bone marrow.

Delivery of oligonucleotides and/or expression vectors to a target cell can be achieved in a variety of ways. In some embodiments, a transfection agent is used. A transfection agent, or transfection reagent or delivery vehicle, is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. Transfection reagents are well known in the art. One transfection reagent suitable for delivery of miRNA is siPORT.TM. NeoFX.TM. transfection agent (Ambion), which can be used to transfect a variety of cell types with miRNA. miRNAs can be readily electroporated into primary cells without inducing significant cell death. In addition, miRNAs can be transfected at different concentrations. The transfection efficiency of synthetic miRNAs has been shown to be very good, and around 100% for certain cell types (Ambion.®. miRNA Research Guide, page 12.).

Reagents for delivery of miRNA, anti-miRNA and expression vectors can include, but are not limited to protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups can include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers). For delivery in vivo, complexes made with sub-neutralizing amounts of cationic transfection agent may be preferred.

In some embodiments, polycations are mixed with polynucleotides for delivery to a cell. Polycations are a very convenient linker for attaching specific receptors to DNA and as result, DNA/polycation complexes can be targeted to specific cell types. Here, targeting is preferably to cells involved in innate immunity. An endocytic step in the intracellular uptake of DNA/polycation complexes is suggested by results in which functional DNA delivery is increased by incorporating endosome disruptive capability into the polycation transfection vehicle. Polycations also cause DNA condensation. The volume which one DNA molecule occupies in complex with polycations is drastically lower than the volume of a free DNA molecule. The size of DNA/polymer complex may be important for gene delivery in vivo. In some embodiments, miR-146 or anti-miR-146 nucleic acids and a transfection reagent are delivered systematically such as by injection. In other embodiments, they may be injected into particular areas comprising target cells, such as particular organs, for example the bone marrow.

Polymer reagents for delivery of miRNA, anti-miRNA and expression vectors may incorporate compounds that increase their utility. These groups can be incorporated into monomers prior to polymer formation or attached to polymers after their formation. A miRNA, anti-miRNA or expression vector transfer enhancing moiety is typically a molecule that modifies a nucleic acid complex and can direct it to a cell location (such as tissue cells) or location in a cell (such as the nucleus) either in culture or in a whole organism. By modifying the cellular or tissue location of the complex, the desired localization and activity of the miRNA, anti-miRNA or expression vector can be enhanced. The transfer enhancing moiety can be, for example, a protein, peptide, lipid, steroid, sugar, carbohydrate, nucleic acid, cell receptor ligand, or synthetic compound. The transfer enhancing moieties can enhance cellular binding to receptors, cytoplasmic transport to the nucleus and nuclear entry or release from endosomes or other intracellular vesicles.

Nuclear localizing signals can also be used to enhance the targeting of the miRNA, anti-miRNA or expression vector into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Compounds that enhance release from intracellular compartments can cause DNA release from intracellular compartments such as endosomes (early and late), lysosomes, phagosomes, vesicle, endoplasmic reticulum, Golgi apparatus, trans Golgi network (TGN), and sarcoplasmic reticulum and could be used to aid delivery of miRNA-146 or anti-miR-146. Release includes movement out of an intracellular compartment into cytoplasm or into an organelle such as the nucleus. Such compounds include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor moieties are any signal that enhances the association of the miRNA, anti-miRNA or expression vector with a cell. Enhanced cellular association can be accomplished by either increasing the binding of the polynucleotide or polynucleotide complex to the cell surface and/or its association with an intracellular compartment, for example: ligands that enhance endocytosis by enhancing binding the cell surface. Cellular receptor moieties include agents that target to asialoglycoprotein receptors by using asialoglycoproteins or galactose residues. Other proteins such as insulin, EGF, or transferrin can be used for targeting. Peptides that include the RGD sequence can also be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to target cells.

The skilled artisan will be able to select and use an appropriate system for delivering miRNA-146, anti-miRNA-146 or an expression vector to target cells in vitro or in vivo without undue experimentation.

Modulation of Immune Cell Function and/or Proliferation miRNA-146 can be used to modulate activity and/or proliferation of immune cells. Development and activity of immune cells can be modulated by administering a miR-146 oligonucleotide or antisense miR-146 to target cells. The target cells may be in a mammal. In some embodiments, the target cells are hematopoietic cells. In other embodiments, miR-146 or anti miR-146 is delivered to bone marrow.

In some embodiments, proliferation of immune cells can be used to measure the effect of miR-146 or antisense miR-146 on immune cells. For example, proliferation and/or activity of B1 B cells, B2 B cells, Marginal Zone B cells, CD8αα+ T cells, Natural Killer cells and/or CD8+ T cells can be measured. Measurements of proliferation can take place in an appropriate spot for each cell type, such as in the bone marrow, thymus, spleen, periphery, peritoneal cavity or lymph nodes, such as peripheral lymph nodes or mesenteric lymph nodes. Measurement of proliferation can be by any method known in the art, for example by FACS analysis.

In some embodiments, miR-146 or antisense miR-146 are administered by administering a miR-146 or anti-miR-146 expression vector to target cells and expressing the desired miR-146 or anti-miR-146 in the target.

In some embodiments, the activity and/or proliferation of certain cells, such as B1 B cells, B2 B cells, Marginal Zone B cells, CD8αα+ T cells, Natural Killer cells and CD8+ T cells is modulated using miR-146 or anti-miR-146. The activity and/or proliferation of these cells can be either upregulated or down-regulated.

In some embodiments, activity and/or proliferation of B1 B cells, Marginal Zone B cells, CD8+ cells and Natural Killer cells can be upregulated by administering a miRNA-146 oligonucleotide or a miRNA-146 expression vector to target cells, organs or tissues. In some embodiments, the miR-146 expression vector comprises a nucleic acid sequence encoding a miRNA-146 operably linked to a U6 promoter or a CMV promoter.

Increased numbers of B1 B cells, Marginal Zone B cells, CD8+ cells and Natural Killer cells can be detected, for example, by FACS analysis after administering a miRNA-146 oligonucleotide or a miRNA-146 expression vector to a target tissue.

In other embodiments, activity and/or proliferation of B1 B cells, Marginal Zone B cells, CD8+ T cells and Natural Killer cells is downregulated by administering an antisense miRNA-146 oligonucleotide or an anti-miR-146 expression vector to target cells or target tissue.

Decreased numbers of B1 B cells, Marginal Zone B cells, CD8+ cells and Natural Killer cells can be detected, for example, by FACS analysis after administering an antisense miRNA-146 oligonucleotide or an antisense miRNA-146 expression vector to a target tissue.

In some embodiments, activity and/or proliferation of B2 B cells and CD8αα+ T cells can be upregulated by administering an antisense miRNA-146 oligonucleotide to target cells or target tissue. In other embodiments, the methods comprise administering an antisense miRNA-146 expression vector to target cells or target tissue and expressing a miRNA-146 in the target. In some embodiments, increased numbers of B2 B cells and CD8αα+ T cells can be detected by FACS analysis after administering an antisense miRNA-146 oligonucleotide or an antisense miRNA-146 expression vector to a target.

Proliferation and/or activity of B2 B cells and CD8αα+ T cells can be downregulated. In some embodiments, the methods comprise administering a miRNA-146 oligonucleotide to a target tissue. In other embodiments, the methods comprise administering a miRNA-146 expression vector to a target tissue and expressing a miRNA-146 in the target tissue. In some embodiments, decreased numbers of B2 B cells and CD8αα+ T cells can be detected by FACS analysis after administering a miRNA-146 oligonucleotide or a miRNA-146 expression vector to a target tissue.

Any of a variety of sequences of miRNA-146 or antisense miRNA-146 can be used to regulate activity and proliferation of various immune cells in the embodiments described above. In some embodiments, the miR-146 oligonucleotide comprises mature all or a portion of miR-146a, mature miR-146b, pre-miR-146a, pre-miR-146b, pri-miR-146a, pri-miR-146b, or a miR-146 seed sequence. Mixtures of various miR-146 nucleic acids can also be used. In some embodiments, the miR-146 comprises all or a portion of a sequence selected from the group consisting of SEQ ID NO: 1, SEQ ID NO: 2, SEQ ID NO: 3, SEQ ID NO: 4 or SEQ ID NO: 14.

In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8.

In some embodiments, the anti-sense miR-146 is complementary to all or a portion of SEQ ID NOs: 1, 2, 3, 4 or 14. In some embodiments the anti-sense miR-146 hybridizes under stringent conditions to one or more of SEQ ID NOs: 1, 2, 3, 4 or 14. In other embodiments the antisense miR-146 comprises a sequence selected from the group consisting of SEQ ID NO: 9 and SEQ ID NO: 10.

In some embodiments, to regulate activity and/or proliferation of certain immune cells, target tissues to which miRNA-146 or antisense miRNA-146 are delivered are hematopoietic tissues. For example, in some embodiments miR-146 oligonucleotides or expression vectors or anti-miR-146 oligonucleotides or expression vectors are preferably delivered to the bone marrow. In other embodiments, targets are tissues or organs comprising immune cells. In other embodiments the miR-146 or anti-miR-146 is delivered directly to the immune cells to be regulated or to precursor cells.

miRNA-146 or antisense miRNA-146 can be delivered as described herein or as known in the art. For example, delivery can be achieved by modification of an oligonucleotide encoding a miR-146, such as a mature miR-146a or miR-146b, with cholesterol to help it easily penetrate the cell membrane. Delivery can be optimized by using modified nucleotides or utilizing backbone modifications. Delivery can be achieved by injection into particular areas such as hematopoietic tissue or the bone marrow.

In other embodiments, miR-146, anti-miR-146 or expression vectors are delivered systemically. miRNA-146 or antisense miRNA-146 can be delivered as described herein or as known in the art. For example, miRNA-146 or antisense miRNA-146 can be delivered in combination with pharmaceutically acceptable carriers. In some embodiments miRNA-146 or antisense miRNA-146 or expression vectors can be injected intravenously.

Modulation of Production of Pro-Inflammatory Cytokines miRNA-146 can regulate production of pro-inflammatory cytokines in immune cells. For example, in some embodiments production of pro-inflammatory cytokines in macrophages is regulated using miR-146 or anti-miR-146. Pro-inflammatory cytokines that can be regulated include, for example, TNFα and IL-6. In some embodiments production of pro-inflammatory cytokines by immune cells is downregulated by modulating levels of miRNA-146a in the immune cells.

In some embodiments, the methods comprise administering a miRNA-146 oligonucleotide to immune cells in which pro-inflammatory cytokine production is to be reduced. In some embodiments, the miR-146 oligonucleotide comprises all or a portion of mature miR-146a, mature miR-146b, pre-miR-146a, pre-miR-146b, pri-miR-146a, pri-miR-146b, or a miR-146 seed sequence. Mixtures of various miR-146 nucleic acids can also be used. In some embodiments, the miR-146 comprises a sequence selected from the group consisting of SEQ ID NO: 1, SEQ ID NO: 2, SEQ ID NO: 3, SEQ ID NO: 4 or SEQ ID NO: 14.

In other embodiments, the methods comprise administering a miRNA-146 expression vector to target cells and expressing a miRNA-146 in target cells to reduce production of pro-inflammatory cytokines. In some embodiments, the miR-146 expression vector comprises a nucleic acid sequence encoding a miRNA-146 operably linked to a U6 promoter or a CMV promoter. In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8.

To reduce production of certain pro-inflammatory cytokines, miRNA-146 can be delivered to immune cells that produce pro-inflammatory cytokines, such as dendritic cells, macrophages, Th1 helper T cells, Th2 helper T cells and regulator T cells. In other embodiments the miR-146 is delivered to precursor cells that develop into immune cells or tissues comprising precursor cells, such as bone marrow. In some embodiments miR-146 is delivered to the cells, tissues comprising the cells or systemically. miRNA-146 or antisense miRNA-146 can be delivered as described herein or as known in the art. For example, in some embodiments the miR-146 oligonucleotide or expression vector can be administered to the cells by transfection. In other embodiments, they may be directly injected into bone marrow. miRNA-146 or antisense miRNA-146 can be modified to enhance delivery. For example, these oligonucleotides can be modified with cholesterol. In other embodiments miRNA-146 or antisense miRNA-146 can be injected into target cells, a tissue comprising the target cells, or injected systemically into a mammal comprising the target cells. miRNA-146 can also be coupled to a ligand of a target cell surface receptor and enter into target cells through endocytosis.

In some particular embodiments, production of pro-inflammatory cytokines by macrophages is reduced by administering miR-146 or a miR-146 expression vector to macrophages or macrophage precursor cells. In other embodiments, macrophage activity is downregulated by administering miR-146 to target tissue, such as bone marrow, or directly to macrophages.

In other embodiments, production of pro-inflammatory cytokines by immune cells can be increased by administering anti-miR-146 or an anti-miR-146 expression vector to the immune cells. The anti-miR-146 can be essentially as described elsewhere herein.

Modulation of T Cell Activation miRNA-146 can also be used to regulate T cell activation. In some embodiments, T cell activation is downregulated by increasing levels of miRNA-146 in T cells. In some embodiments, the methods comprise administering a miRNA-146 oligonucleotide to target T cells or precursor cells. In other embodiments, the methods comprise administering a miRNA-146 expression vector to target T cells or precursor cells and expressing a miRNA-146 in the target cells. In some embodiments the miR-146 oligonucleotide or expression vector are delivered to tissues or organs comprising T cells or precursor cells, such as bone marrow. In some embodiments, the miR-146 expression vector comprises a nucleic acid sequence encoding a miRNA-146 operably linked to a U6 promoter or a CMV promoter. T cell activation can be measured by any method known in the art, for example by measuring surface expression various markers of activation. For example, activation can be determined by increased surface expression of CD25, CD44 and CD69 proteins and a decrease in CD62L expression, as discussed in the examples below.

In other embodiments, T cell activation can be upregulated by reducing levels or activity of miRNA-146 in target T cells. In some embodiments, the methods comprise administering an antisense miRNA-146 oligonucleotide to target T cells. In other embodiments, the methods comprise administering an antisense miRNA-146 expression vector to target T cells and expressing an antisense miRNA-146 in the target cells.

In some embodiments, the miR-146 oligonucleotide comprises all or an effective portion of mature miR-146a, mature miR-146b, pre-miR-146a, pre-miR-146b, pri-miR-146a, pri-miR-146b, or a miR-146 seed sequence. Mixtures of various miR-146 nucleic acids can also be used. In some embodiments, the miR-146 comprises all or an effective portion of a sequence selected from the group consisting of SEQ ID NO: 1, SEQ ID NO: 2, SEQ ID NO: 3, SEQ ID NO: 4 or SEQ ID NO: 14. In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8.

In some embodiments, the antisense miR-146 comprises a sequence that is complementary to a miR-146 oligonucleotide as discussed above, or that hybridizes under stringent conditions to a miR-146 oligonucleotide. In some embodiments the anti-miR-146 is selected from the group consisting of SEQ ID NO: 9 and SEQ ID NO: 10.

Target T cells can be, for example and without limitation, Th1 helper T cells, Th2 helper T cells and regulator T cells. Target cells may also be precursor cells. As described above, the target may also be tissue, such as bone marrow, that comprises T cells or precursor cells. miRNA-146, antisense miRNA-146 and expression vectors can be delivered as described herein or as known in the art. For example, a miR-146 oligonucleotide or expression vector can be administered to the cells by transfection. miRNA-146 or antisense miRNA-146 can be modified to enhance delivery. For example, they can be modified with cholesterol. miRNA-146 or antisense miRNA-146 or expression vectors can also be injected into target cells. miRNA-146 or antisense miRNA-146 can also be coupled to a ligand of a target cell surface receptor and enter into target cells through endocytosis. In some embodiments the miR-146, anti-miR-146 or expression vector is delivered systemically, or injected into organs or tissues comprising target T cells. For example, miRNA-146, anti-miR-146 or expression vectors can be delivered to target tissues such as bone marrow, spleen or other peripheral immune tissues.

Modulation of Certain Kinase Activation miRNA-146 can also be used to regulate activation of certain kinases such as NF-kB, JNK1 or ERK in immune cells. In some embodiments the activation of these kinases can be downregulated by modulating levels of miRNA-146 or miR-146 activity in target immune cells or immune precursor cells.

In some embodiments, miRNA-146 can be used to down-regulate activation of NK-kB and/or JNK1 in immune cells. In some embodiments, the methods comprise administering a miRNA-146 oligonucleotide to target immune cells, precursor cells or tissue, such as bone marrow. In other embodiments, the methods comprise administering a miRNA-146 expression vector to target immune cells and expressing a miRNA-146 in the target cells.

In other embodiments, antisense miRNA-146 can be used to down-regulate activation of ERK in immune cells. In some embodiments, the methods comprising administering an antisense miRNA-146 oligonucleotide to target immune cells. In other embodiments, the methods comprise administering an antisense miRNA-146 expression vector to target immune cells and expressing an antisense miRNA-146 in the target cells.

In some embodiments, the miR-146 or antisense miR-146 expression vector comprises a nucleic acid sequence encoding a miRNA-146 or antisense miR-146 operably linked to a U6 promoter or a CMV promoter.

In some embodiments, the miR-146 oligonucleotide comprises all or an effective portion of mature miR-146a, mature miR-146b, pre-miR-146a, pre-miR-146b, pri-miR-146a, pri-miR-146b, or a miR-146 seed sequence. Mixtures of various miR-146 nucleic acids can also be used. In some embodiments, the miR-146 comprises all or an effective portion of a sequence selected from the group consisting of SEQ ID NO: 1, SEQ ID NO: 2, SEQ ID NO: 3, SEQ ID NO: 4 or SEQ ID NO: 14. In some embodiments, the miR-146 expression vector comprises a sequence encoding a miRNA-146 selected from the group consisting of SEQ ID NO: 5, SEQ ID NO: 6, SEQ ID NO: 7 or SEQ ID NO: 8.

In some embodiments, the antisense miR-146 comprises a sequence that is complementary to a miR-146 oligonucleotide as discussed above, or that hybridizes under stringent conditions to a miR-146 oligonucleotide. In some embodiments the anti-miR-146 is selected from the group consisting of SEQ ID NO: 9 and SEQ ID NO: 10.

Immune target cells include, for example and without limitation, dendritic cells, macrophages, Th1 helper T cells, Th2 helper T cells regulator T cells. Target tissue includes, for example, bone marrow. miRNA-146 and anti-miR-146 can also be delivered to target tissues comprising immune cells or precursor cells. In some embodiments miR-146 is delivered to the cells, tissues comprising the cells or systemically. In some embodiments miR-146 or anti-miR-146 are delivered to hematopoietic tissue, such as bone marrow.

miRNA-146, antisense miRNA-146 and expression vectors can be delivered as described herein or as known in the art. For example, delivery of these oligonucleotides can be enhanced by modification with cholesterol. They can be injected to the blood surrounding the target tissue.miRNA-146, antisense miRNA-146 and expression vectors can be delivered as described herein or as known in the art.

Vaccination miRNA-146 can be used to enhance vaccination in a target mammal, such as cancer vaccination. That is, the desired effects of vaccination can be improved by modulating levels of miRNA-146 in target immune cells. Reducing levels of miRNA-146 or miR-146 activity can increase the number and/or activity of CD8αα+ T cells, which can in turn increase the desired immune response to a vaccine.

In some embodiments, the methods comprise administering an antisense miRNA-146 oligonucleotide to a mammal to be vaccinated prior to, concurrent with, or following vaccination with an antigen. In other embodiments, the methods comprise administering an antisense miRNA-146 expression vector to a mammal and expressing an antisense miRNA-146 in immune cells. In some embodiments, the antisense miR-146 or antisense miR-146 expression vector are delivered systemically. In other embodiments, delivery is to target cells or tissues, such as to bone marrow. In some embodiments, the miR-146 expression vector comprises a nucleic acid sequence encoding a miRNA-146 operably linked to a U6 promoter or a CMV promoter. In some embodiments, the antisense miR-146 expression vector comprises a sequence encoding an antisense miRNA-146 selected from the group consisting of SEQ ID NO: 9 and SEQ ID NO: 10.

In some embodiments, anti-miR-146 is delivered to target tissues, such as tissue comprising immune cells or immune precursor cells. In some embodiments the anti-miR-146 is delivered to hematopoietic tissue, such as bone marrow. Anti-miR-146 or vectors for expressing anti-miR-146 can be delivered as described herein or as known in the art. In some embodiments they are delivered into or in proximity of the target tissue. In other embodiments they are delivered systemically. Anti-miR-146 or anti-miR-146 expression vectors can be delivered in combination with pharmaceutically acceptable carriers.

In some embodiments, the antisense miR-146 comprises a sequence that is complementary to at least a portion of a miR-146 oligonucleotide as discussed above, or that hybridizes under stringent conditions to a miR-146 oligonucleotide. In some embodiments the anti-miR-146 is selected from the group consisting of SEQ ID NO: 9 and SEQ ID NO: 10.

The following examples are offered by way of illustration and not by way of limitation.

Knock-Out Mice

Knockout (KO) mice were produced to investigate the biological role for miR-146a miRNA. A mir-146a KO mouse was generated by deleting a 295 bp fragment containing precursor sequence of this miRNA (FIG. 1).

Briefly, a targeting construct was created wherein a 295 bp of genomic sequence containing mouse pre-miR-146a was replaced with a floxed neomycin expression cassette. The assembly of the targeting construct was done by recombineering in bacteria following the protocol established by Copeland et al. Copeland et. al., Nat Rev Genet 2, 769-779. The linearized targeting construct was then electroporated into a 129/SvJ ES cell line and NeoR clones that have undergone homologous recombination were determined by Southern blotting. The resulting targeted ES clones were injected into C57BL/6 blastocysts that were used to produce chimeric mice. Gerline-competent chimeras were then used to produce heterozygous F1 litters, which were then bred to homogeneity. Mice obtained were analyzed in a fashion similar to what is described in the bone marrow transfer experiments. The miR-146$^{-/-}$ mice were born in Mendelian ratios, and they appeared morphologically normal and fertile. As expected, no expression of mature miR-146a was observed in tissues of the KO mice (FIG. 1B and FIG. 1C). In addition, bone marrow derived macrophages (BMDMs) from KO mice have significantly higher expression of TRAF6 protein, an observation that is consistent with previous finding of TRAF6 as a miR-146a target gene (Taganov et al., 2006).

Figure 3C:
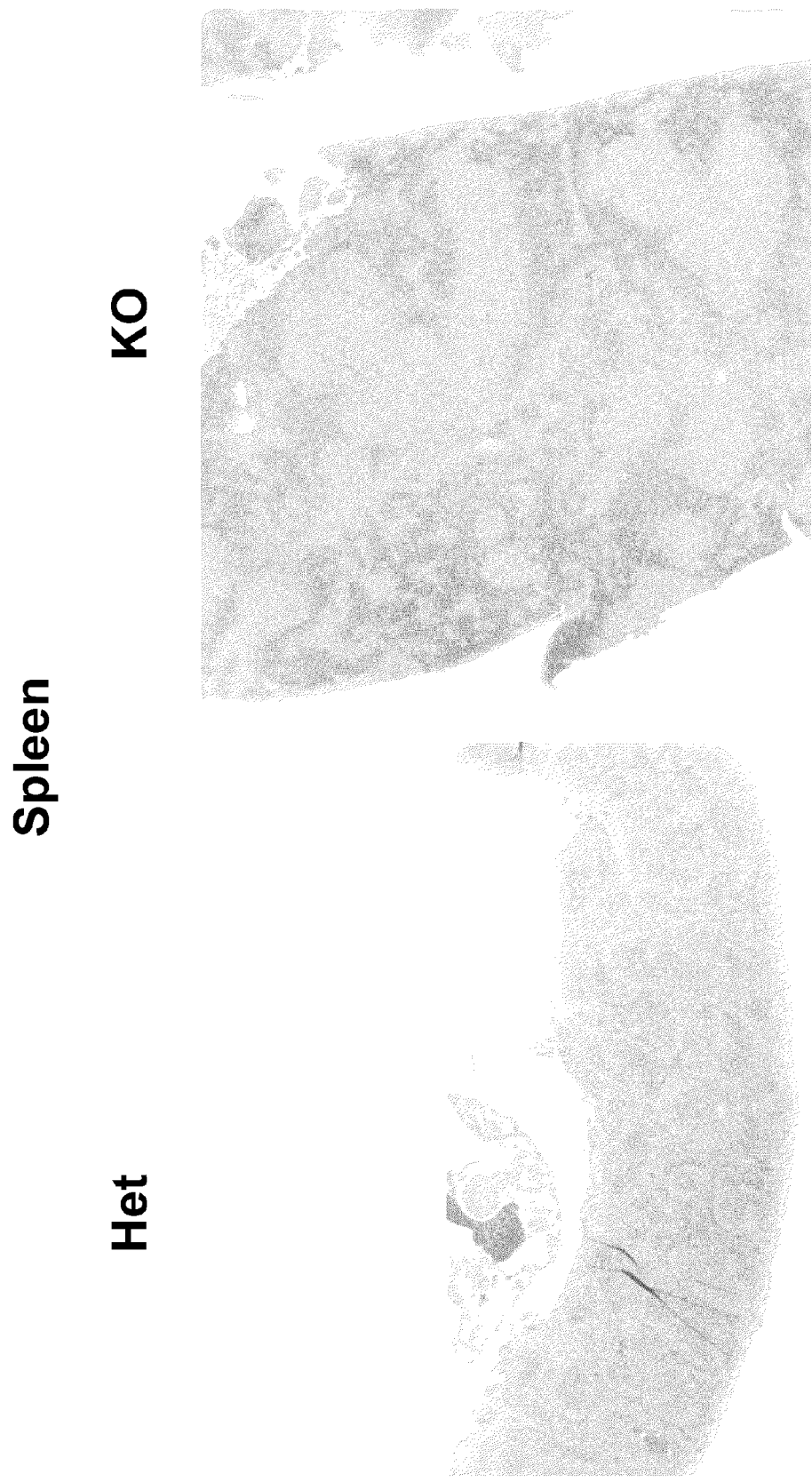
FIG. 3 shows miR-146a KO mice develop multiorgan inflammation and follicular hyperplasia in the spleen. Hematoxylin-eosin (H&E) staining of liver (A) and kidney (B) sections from WT and KO mice. Arrows point to lymphocytic infiltrates. (C). H&E staining of spleen sections at 20× magnification. Note increased number and size of lymphoid follicles and their rugged edges in the KO.
Figure 4:
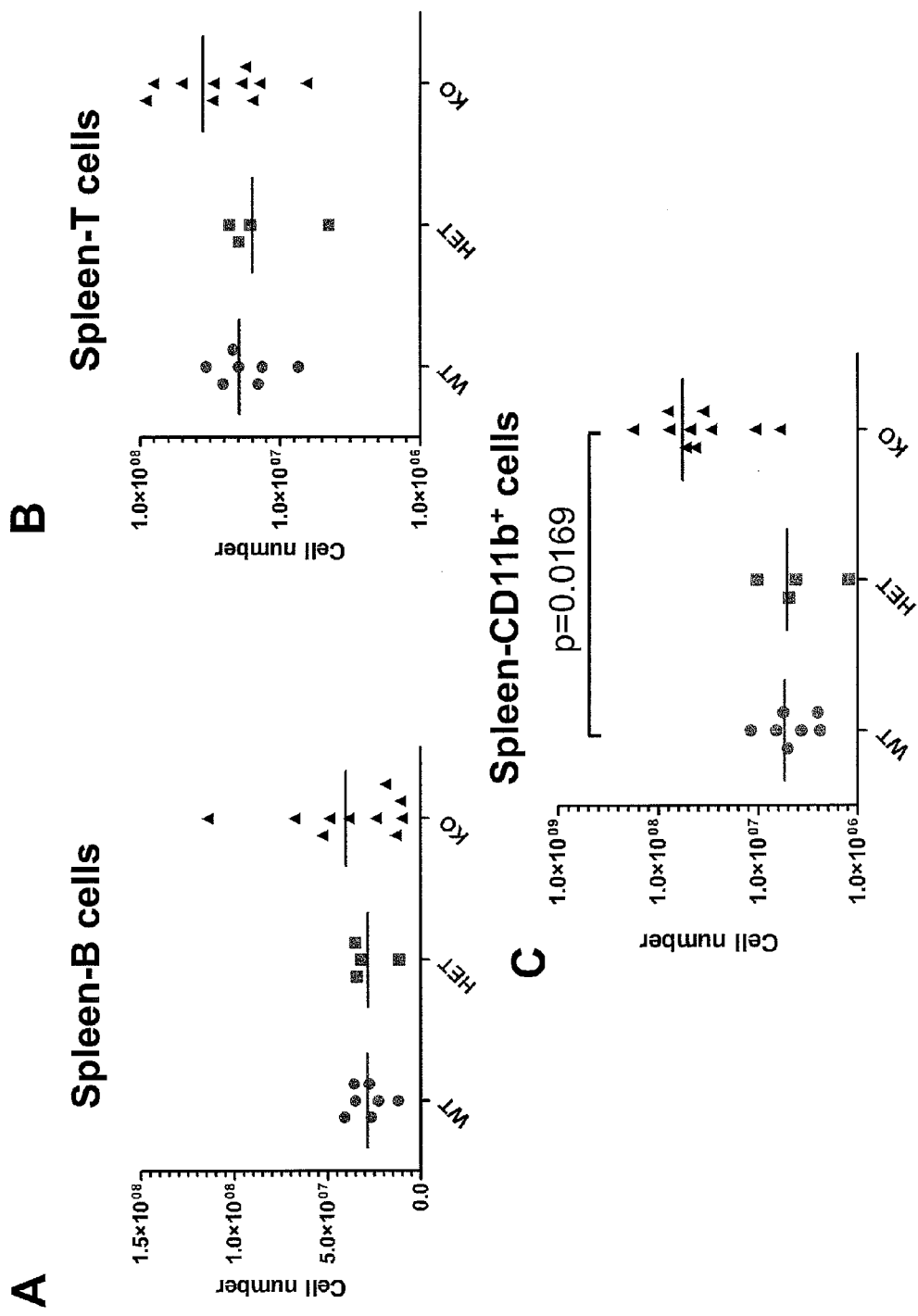
FIG. 4 shows massive myeloproliferation in the spleen of miR-146a KO mice. Absolute cell number of B(A), T(B) and myeloid (C) cells in the spleens of WT, HET and KO mice.
Figure 5A:
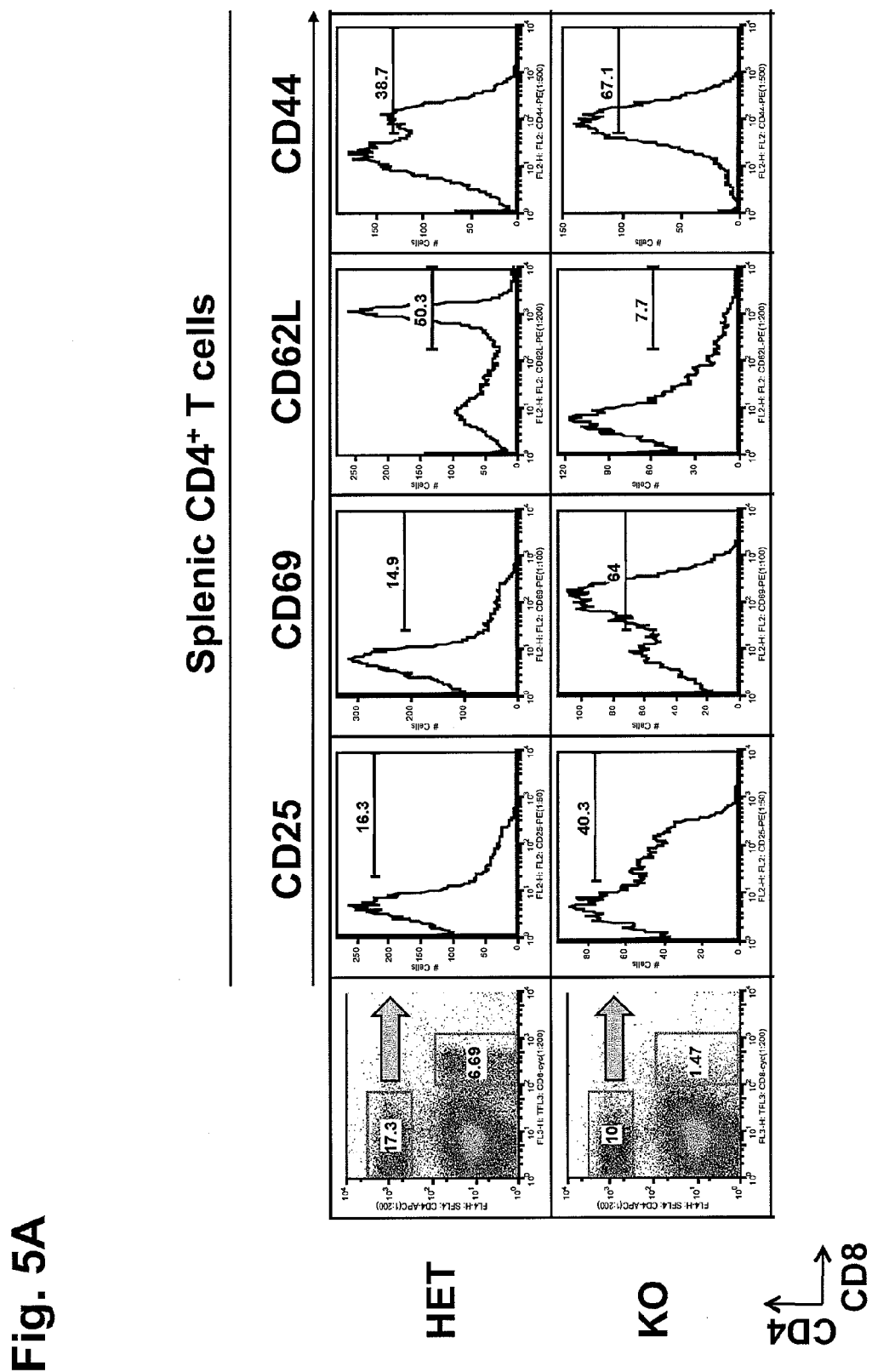
FIG. 5 shows T cell development in miR-146a KO mice. (A). Peripheral T cells of the miR-146a KO mice display an activated status. FACS analysis of CD4-positive T cells for the expression of CD25, CD69, CD62L and CD69 surface markers. (B). FACS analysis of T cell populations in the thymus of WT and KO mice.

Starting at about 6 month of age miR-146a KO mice developed an autoimmune-like disorder that was characterized by splenomegaly and lymphoadenopathy, and as a result died prematurely (FIG. 2A, B). Histological examination of miR-146a KO mice revealed severe inflammation and tissue damage in several peripheral organs, including liver, kidneys and lungs (FIG. 3A, B). The enlarged spleens of the KO mice showed signs of follicular hyperplasia with an increase in the number and size of lymphoid follicles that resulted in squeezing of the red pulp and the marginal zone (FIG. 3C). Flow cytometric analysis of miR-146a KO spleens revealed a massive myeloproliferation with the number of CD11b-positive cells increasing about 10 fold on average (FIG. 4C), while the number of the splenic B and T cells did not change significantly. Peripheral T cells (both CD4 from the KO animals consistently showed an activated, effector status manifested by an increase in the cell surface expression of CD25, CD44 and CD69 proteins and a decrease in CD62L expression (FIG. 5A).

Figure 5B:
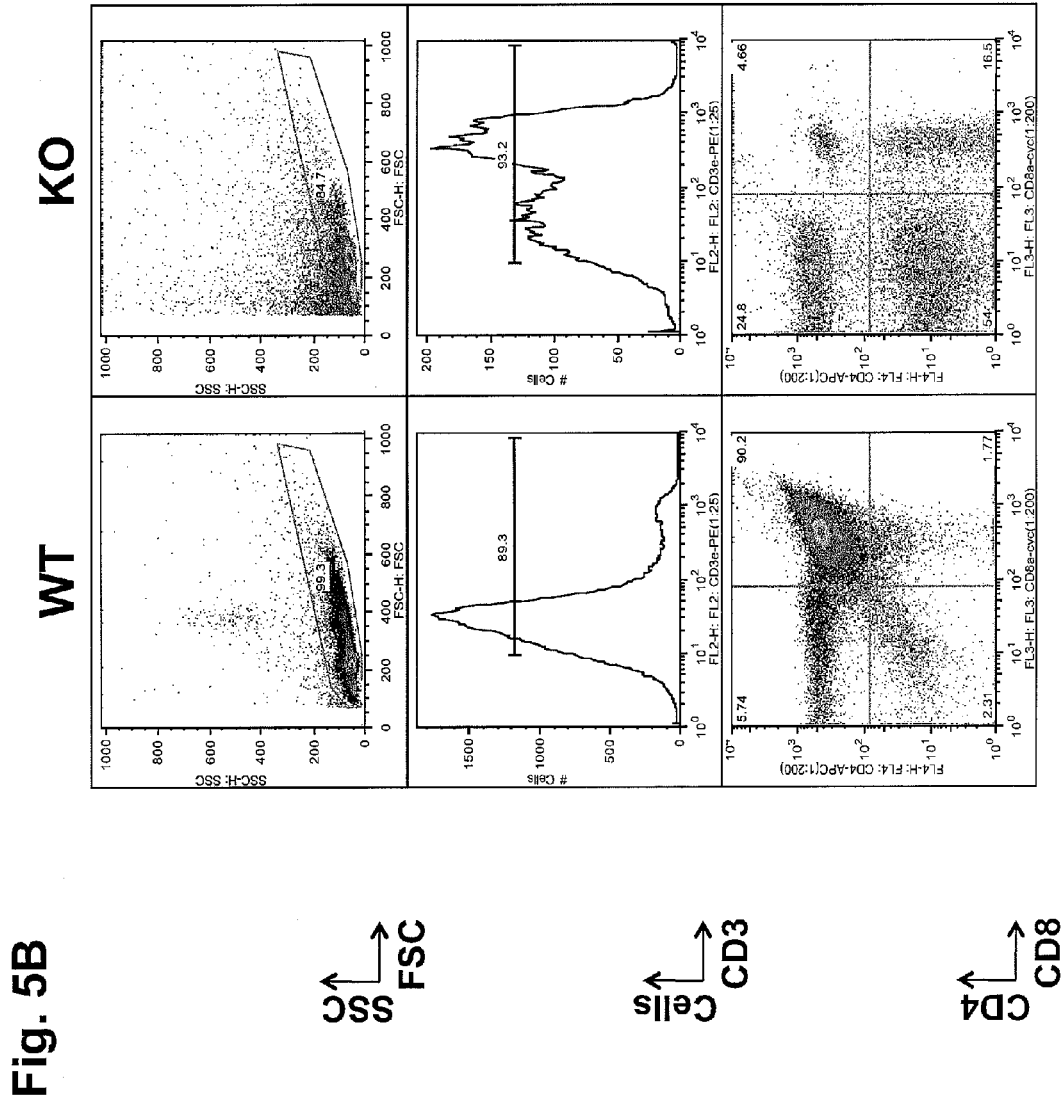

The activated status of peripheral T cells is a characteristic for many autoimmune/inflammatory diseases, where T cells cause damage to peripheral tissues in response to autoantigen stimulation and correlates well with the histological findings of severe inflammation in the miR-146a KO mice. Besides, T cell development in the thymus of KO mice was found to be dysregulated: a dramatic decrease in the number of double positive (CD4+CD8+) thymocytes and an increase in the number of single positive (both CD4+ and CD8+) cells (FIG. 5B) were observed, indicating that the negative T cell selection stage is compromised and is probably a reason for the presence of autoreactive T cells in the periphery.

Figure 6:
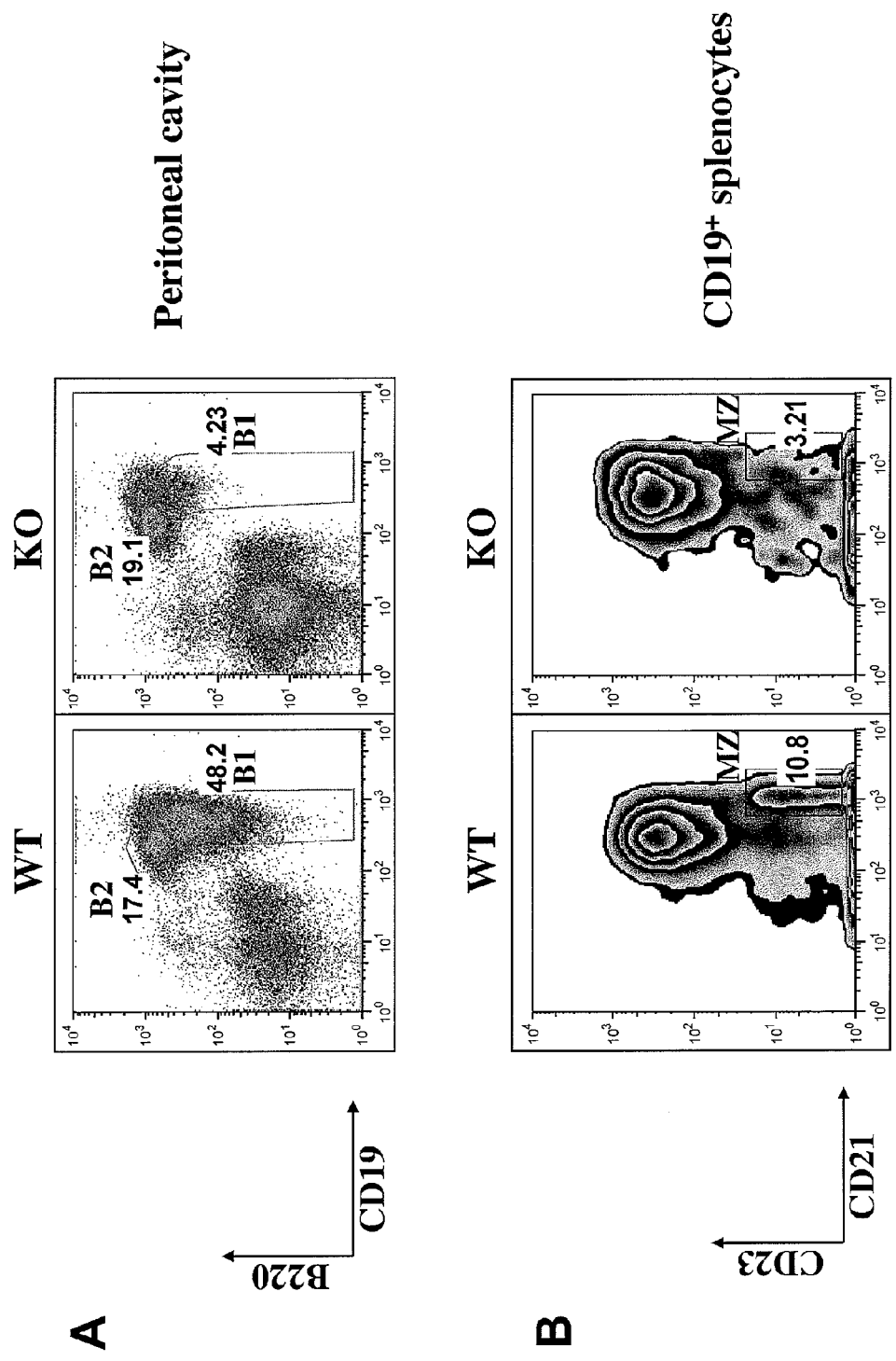
FIG. 6 shows the effect of lack of miR-146a expression on development of several hematopoietic cell lineages in mice. (A). Reduction in B1 B cells numbers in the peritoneal cavity of miR-146a KO mice. B1 B cells are $CD19^+B220^{lo}$ cells as determined by FACS analysis. (B). Reduction of marginal zone B cell population ($CD19^+CD21^+CD23^-$) in the spleen of miR-146a KO mice.
Figure 7:
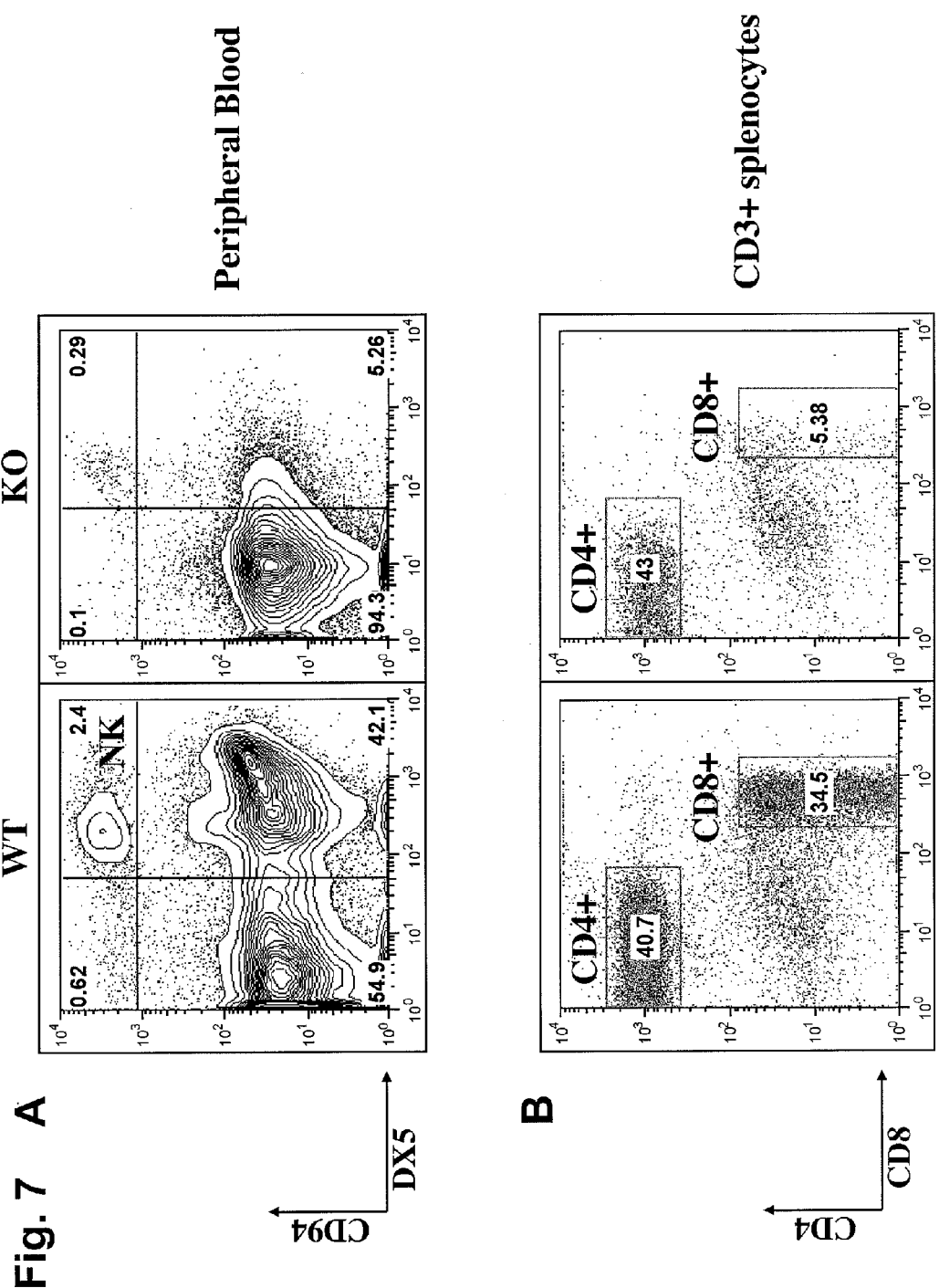
FIG. 7 shows the effect of miR-146a on development of NK and CD8αα lineages. (A) FACS analysis of NK (DX5+ CD94+) cells in the peripheral blood. (B). FACS analysis of CD8αα+ T cells in the peripheral lymph nodes of miR-146a KO mice and WT control.
Figure 8:
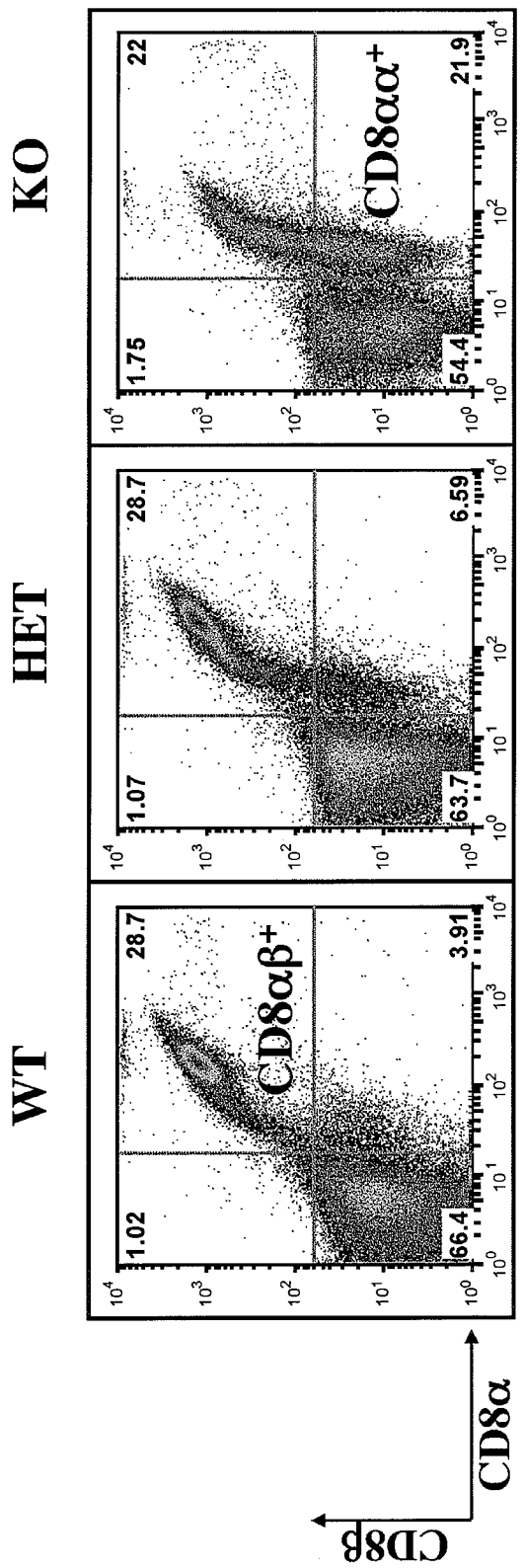
FIG. 8 shows miR-146a plays a negative role in the development of CD80αα T cells. FACS analysis of CD80αα population in the peripheral lymph nodes of WT and KO animals.

Systematic FACS analysis of cells from the KO animals revealed that deletion of miR-146a gene affected development and function of a number of cell lineages of hematopoietic origin. For example, the number of B1 B cells in peritoneal cavity of miR-146a KO animals was markedly reduced (FIG. 6A) and a decrease in the number of marginal zone B cells in the spleen was observed (FIG. 6B). Moreover, miR-146a KO animals have fewer CD8-positive and natural killer (NK) cells in the periphery (FIG. 7). Finally, a dramatic increase in the number of CD8αα+ T cells in the peripheral lymph nodes of miR-146a KO mice was observed in comparison to control (FIG. 8).

Figure 9:
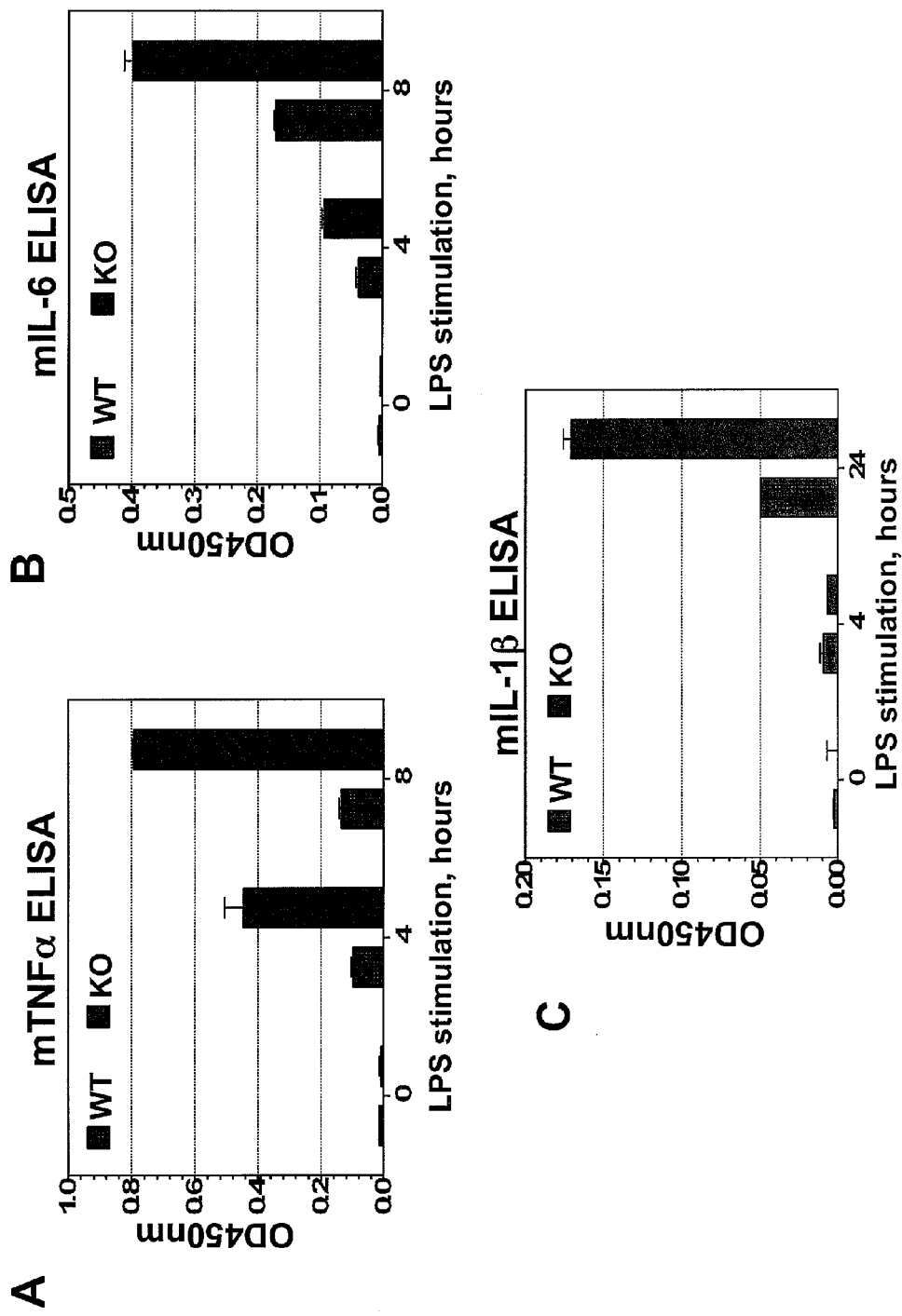
FIG. 9 shows analysis of proinflammatory cytokine production by ELISA using bone marrow-derived macrophages from WT (red bars) and KO (blue bars) animals. (A). Mouse TNFa ELISA. (B) Mouse IL-6 ELISA. (C). Mouse IL-1b ELISA.

The development and function of macrophages with genetically altered levels of miR-146a expression was also examined. Bone marrow-derived macrophages from the KO animals secret significantly higher levels of proinflammatory cytokines, including TNFα, IL-6 and IL-1β after LPS stimulation, indicating that miR-146a plays a role of negative regulator of inflammation and macrophage function (FIG. 9).

Lack of mir-146a Expression Affects Development of Several Hematopoietic Cell Lineages in Mice Multiple hematopoietic cell lineage cells were collected from the miR-146 knockout mice and analyzed by FACS. The FACS analysis was performed by using combinations of antibodies against lineage-specific cell surface markers, and analyzed on a Becton Dickinson FACS Balibur. The results are shown in FIG. 2. The number of B1 B cells in peritoneal cavity of the miR-146a knockout mice was markedly reduced (~4.5 folds). In contrast, the total number of conventional B2 cells has modestly increased (~25-40%). CD8$^+$ and NK cells are also studied. A drop in the number of these T cells was detected in miR-146a knockout mice in thymus and peripheral lymphoid organs. Analysis of the marginal zone B cells in spleen in the miR-146a knockout mice revealed a severe reduction in number of the cells comparing to the wild-type control. In addition, a dramatic increase in the number of CD8αα+ T cells in the peripheral lymph nodes of the miR-146a knockout mice was observed.

Bone Marrow Transfer (BMT) Experiments 5-fluorouracil (5-FU) enriched bone marrow-derived hematopoietic stem cells (HSC) from C57BL/6 mouse were infected with a retrovirus carrying a miR-146a expression cassette (or control virus) and transplanted into lethally γ-irradiated C57BL/6 recipient mice. Eight mice were transplanted and analyzed for each miRNA construct or control construct. Secondary bone marrow transfer experiments were carried in a similar fashion, except infection of HSCs was not applied.

The transduced HSCs and their progenitors were traced by expression of green fluorescent protein (GFP), which was inserted into the retrovirus upstream of the miR-146a cassette under the control of mouse stem cell virus (MSCV) LTR. Hematopoietic organs and tissues from miR-146a-expressing and control mice were collected 2-3 months post transplantation and subjected to a quantitative RT-PCR analysis to determine the level of miR-146a expression as well as FACS analysis using combinations of antibodies against lineage-specific cell surface markers. To perform the RT-PCR analysis, total RNA was isolated using mirVana miRNA Isolation kit (Ambion). miRNA expression was measured with Mir-Vana qRT-PCR miRNA Detectin kit (Ambion) according to vendor protocol and normalized by 5S rRNA levels.

Figure 11:
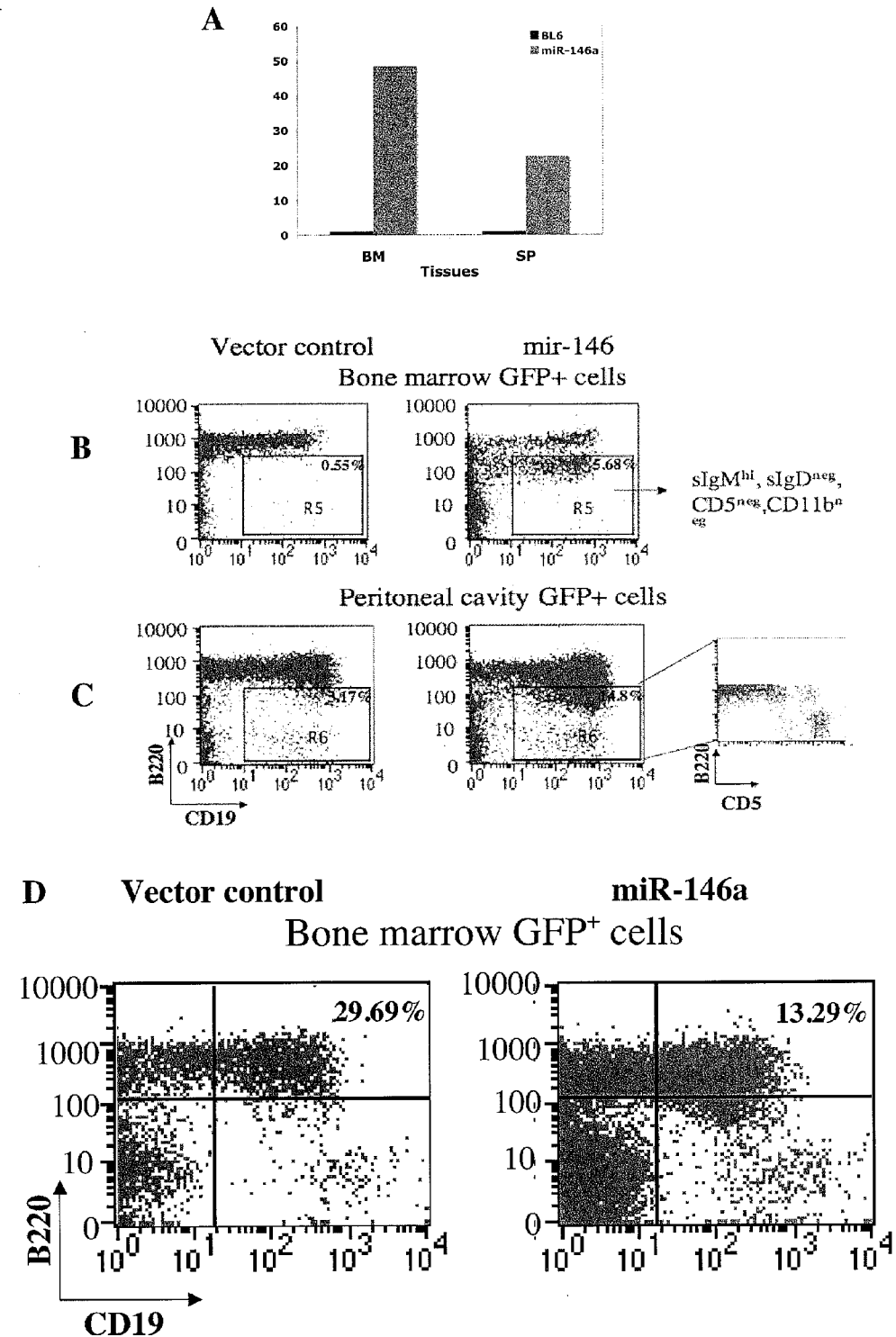
FIG. 11 shows that expression of miR-146a in hematopoietic system affects development of some B and T cell subsets. (A) miR-146 expression levels as determined by quantitative RT-PCR analysis of hematopoietic tissues of miR-146a-expressing and control mice collected 2-3 months post transplantation. (B) FACS analysis of GFP-positive B1 B cells from bone marrow of BMT mice. (C) FACS analysis of GFP-positive cells from peritoneal cavity of BMT mice. The $CD19^+B220^{lo-neg}$ population was analyzed further for CD5 expression. (D). B cell development in the bone marrow. (E). Staining for CD8+ T cells (CD8+ CD3+) cells in the spleen. (F). Staining for CD8αα cells in the mesenteric lymph nodes (MLN).
Figure 11:
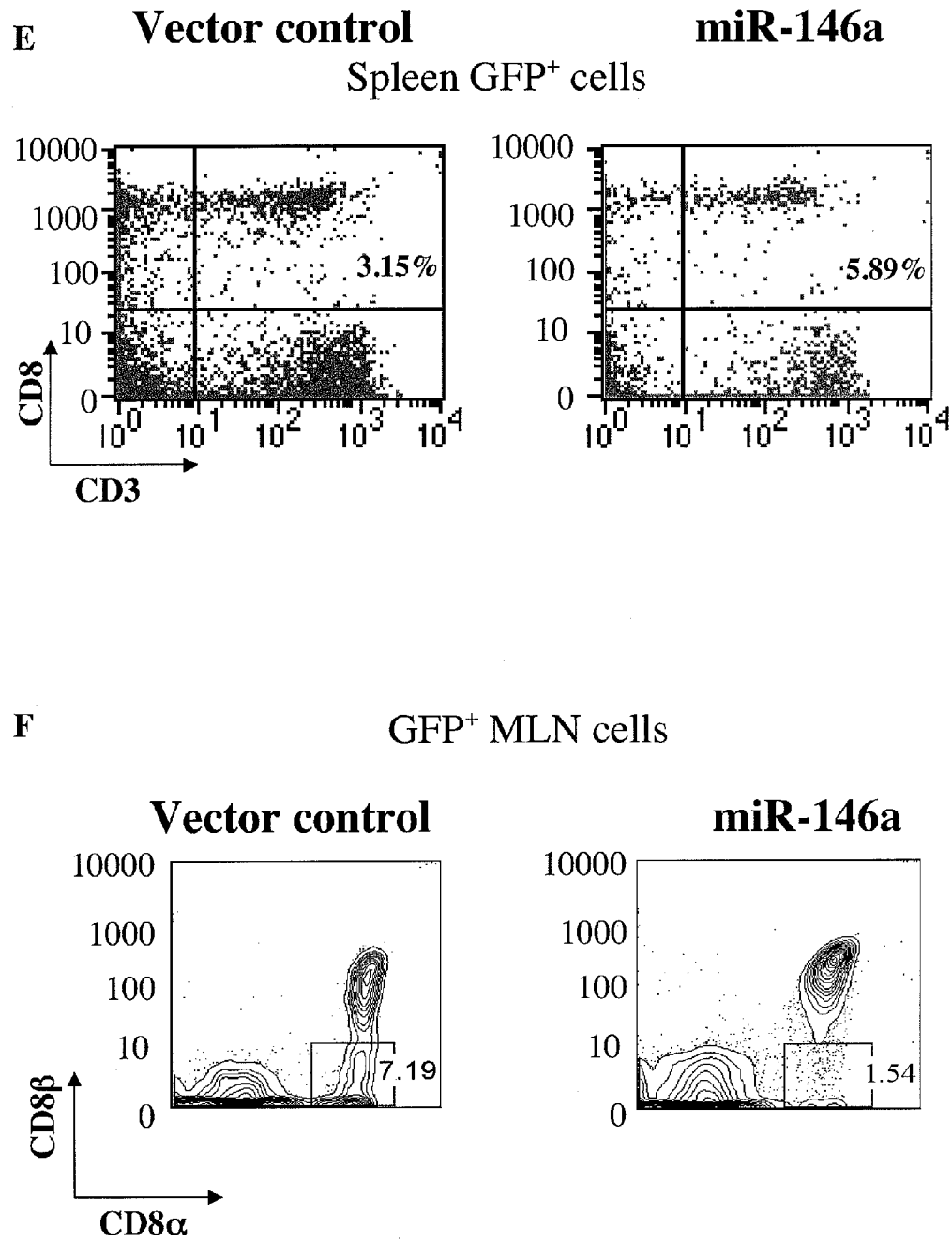

A high level of repopulation of the primary and secondary lymphoid organs by GFP-positive cells were found in both control and miR-146a mice and a strong expression of mature miR-146A was found in the bone marrow (~50 fold increase over control) and in the periphery (~20 fold increase over control in spleen) of miR-146a-overexpressing animals (FIG. 11A). Analysis of multiple hematopoietic cell lineages in miR-146a-overexpressing mice revealed a dramatic increase (~10 fold) in numbers of B-1 B precursor cells (B220$^{lo-neg}$ CD19$^+$ IgD$^{lo}$ IgM$^{high}$) in the bone marrow compartment, which was mirrored by a significant elevation in numbers of mature B-1 B cells in the peritoneal cavity (FIG. 11B). Analysis of the transplanted animals over a period of one month revealed an inverse correlation over time between the number of B-1 B precursor cells in the bone marrow compartment and the number of mature B cells in the periphery. In addition, analysis of miR-146a-expressing animals revealed a significant drop in the number of B2 cells in bone marrow. A reduction in the number of CD8αα T cells in the mesenteric lymph nodes was also observed while the number of CD8$^+$CD3$^+$ conventional T cells in spleen was increased (FIG. 11 E, F).

Overexpression of mir-146a in Human Monocytic THP-1 Cell Line

Figure 10:
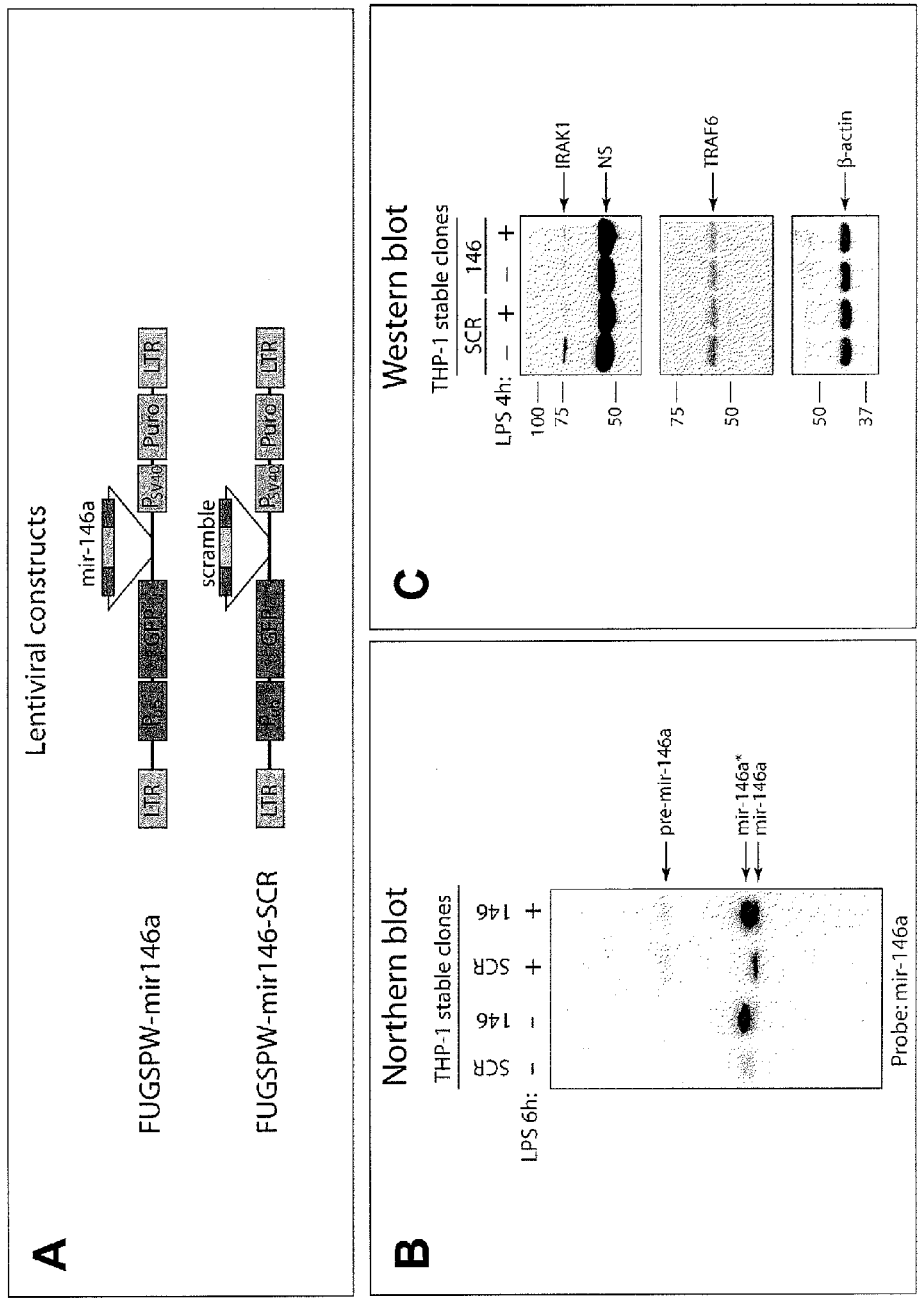
FIG. 10 shows that miR-146a overexpression downregulates levels of endogenous TRAF6 and IRAK1 proteins and suppresses production of proinflammatory cytokines in stable THP-1 cell lines. (A). Schematic diagram of lentiviral constructs used to establish stable THP-1 lines. (B). Northern blot analysis of miR-146a expression in the established THP-1 cells. miR-146a marks the band corresponding to mature exogenous miR-146a. (C). Western blot analysis of human IRAK1 and TRAF6 protein expression in the established THP-1 cell lines. (D). Western blot analysis of LPS-induced activation of NF-kB, JNK and ERK pathways in the established THP-1 lines. pJNK1-stands for phospho-JNK1; pERK1/2- denotes phospho-ERK1/2. (D). Analysis of hTNFa, hIL-6 and hIL-8 secretion by ELISA in the media of LPS-stimulated THP1/SCR and THP1/146 cells. (E) Analysis of cytokine production in response to LPS challenge.
Figure 10:
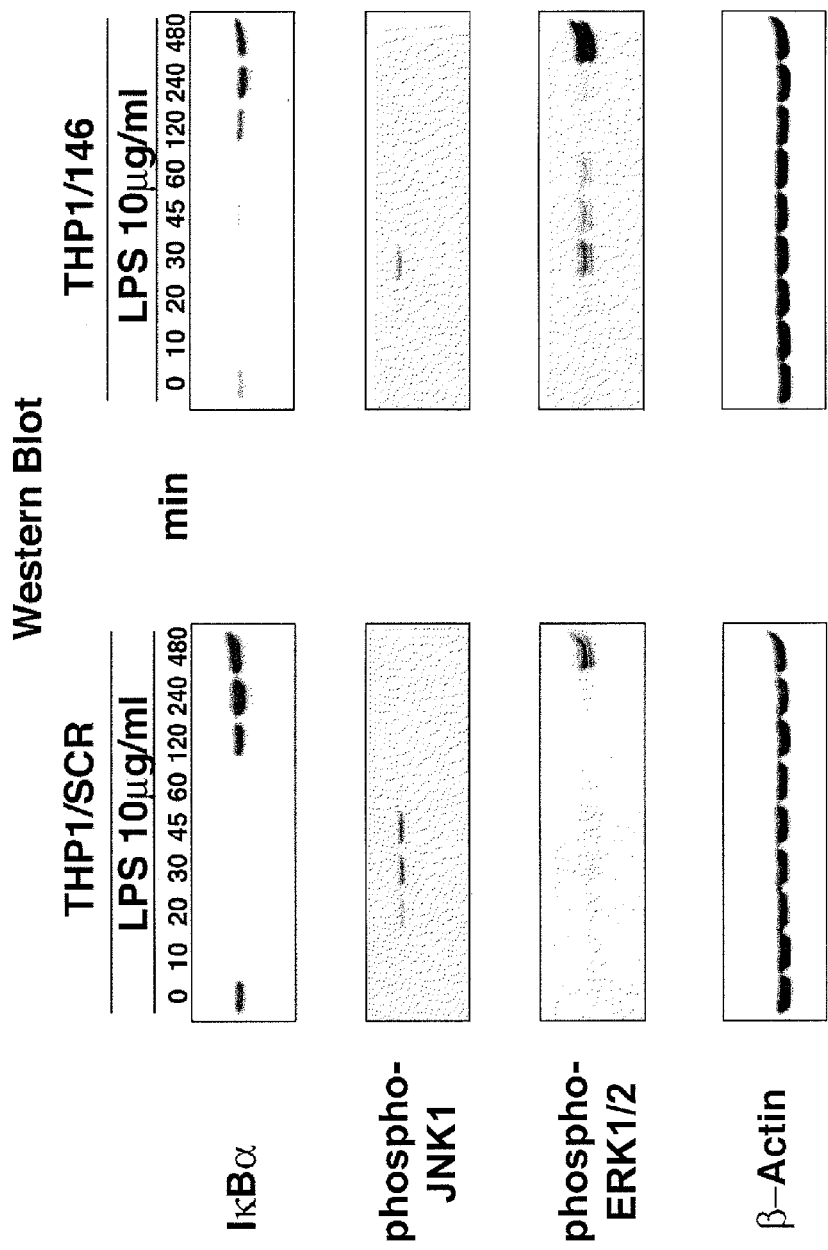
Figure 10:
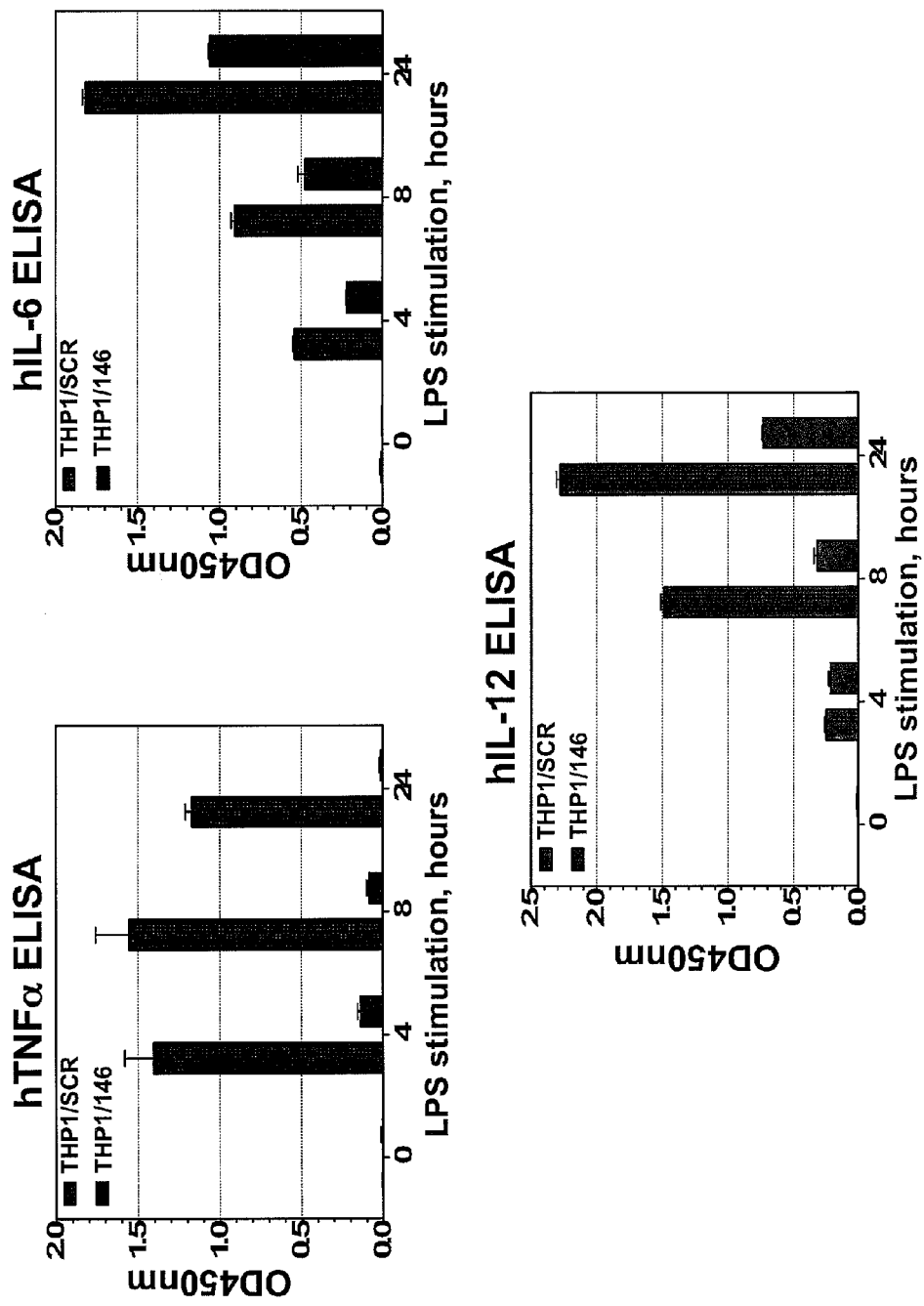

Enforced expression of miR-146a in human monocytic THP-1 cell line confirmed that miR-146a could modulate cytokine production in response to LPS challenge (FIG. 10E). A miR-146a-overexpressing THP-1 line (THP/146) was established that produced approximately 8 fold more mature miR-146 than THP/SCR control cells (FIG. 10B). Enforced expression of miR-146a in human monocytic THP-1 cell line could indeed modulate response to LPS challenge. The increase in miR-146 amounts in THP/146 cells correlated with a significant drop in protein levels of IRAK1 and a somewhat smaller effect (~30-40%) on TRAF6 protein (FIG. 10C). The observed change in the levels of these two adapter proteins had a strong functional consequence—miR-146a expressing cells (THP/146) secreted much less proinflammatory cytokines in comparison to control (THP/SCR) after LPS treatment. The effects of miR-146a overexpression on TLR4 signaling in these two lines were also examined by assessing the activation of three major kinase cascades downstream of TLRs: the NF-kB, JNK and ERK activation pathways. Constitutive miR-146a overexpression resulted in attenuated NF-kB activation as can be seen from changed kinetics of IkBa degradation and resynthesis (FIG. 10D). JNK1 kinase activation was also negatively affected in THP/146 cells, while activation of ERK1 pathway, in contrast, was upregulated. These results suggest that miR-146a plays an important role in fine-tuning TLR signaling by affecting expression of TRAF6 and IRAK1 at the protein level.

Although the foregoing invention has been described in terms of certain embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims. All references cited herein are incorporated by reference in their entirety.

What is claimed is:

1. A method of modulating development of immune cells in a mammal comprising:
   administering a miR-146 oligonucleotide to an immune precursor cell or a hematopoietic cell in the mammal whereby the immune precursor cell or a hematopoietic cell expresses a miR-146 and develops into one or more immune cells, wherein administering a miR-146 oligonucleotide comprises administering a miR-146 expression vector to the immune precursor cell or the hematopoietic cell; and
   measuring proliferation of one or more B1 B cells, marginal zone B cells, CD8+cells, B2 cells, CD8αα cells, or natural killer cells in the mammal.

2. The method of claim 1, wherein the miR-146 oligonucleotide comprises a nucleic acid sequence encoding a miR-146 selected from the group consisting of ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 14.

3. The method of claim 1, wherein the miR-146 oligonucleotide is administered to the hematopoietic cell.

4. The method of claim 1, wherein administering the miR-146 oligonucleotide to the immune precursor cell or the hematopoietic cell increases proliferation or activity of the one or more immune cells developed from the immune precursor cell or the hematopoietic cell.

5. The method of claim 1, wherein administering the miR-146 oligonucleotide to the immune precursor cell or the hematopoietic cell reduces pro-inflammatory cytokine production of the one or more immune cells developed from the immune precursor cell or the hematopoietic cell.

* * * * *

UNITED STATES PATENT AND TRADEMARK OFFICE
CERTIFICATE OF CORRECTION

PATENT NO. : 9,090,894 B2
APPLICATION NO. : 12/337525
DATED : July 28, 2015
INVENTOR(S) : David Baltimore et al.

It is certified that error appears in the above-identified patent and that said Letters Patent is hereby corrected as shown below:

ON THE TITLE PAGE

Page 1 (item 73, Assignee) at line 2, Change "Pasedena," to --Pasadena,--.

In column 2 (page 1, item 56) at line 3, Under Other Publications, change "Hetatology," to --Hepatology,--.

In column 2 (page 1, item 56) at line 14, Under Other Publications, change "CD8alpha alpha" to --CD8αα--.

IN THE DRAWINGS

Sheet 12 of 16 (Fig. 10) at line 3 (approx.), Change "mir146a" to --mir-146a--.

Sheet 12 of 16 (Fig. 10) at line 5 (approx.), Change "mir146" to --mir-146--.

IN THE SPECIFICATION

In column 1 at lines 16-18, Under STATEMENT REGARDING FEDERALLY SPONSORED R&D, Change "The U.S. Govement has certain rights in this invention pursuant to Grant No. GM039458 awarded by National Institues of Health." to --This invention was made with government support under Grant No. GM039458 awarded by the National Institutes of Health. The government has certain rights in the invention--.

In column 4 at line 12 (approx.), Change "antisense-miR146" to --antisense miR-146--.

In column 4 at lines 41-42, Change "lymphoadenopathy." to --lymphadenopathy.--.

In column 5 at line 7, Change "CD80αα" to --CD8αα--.

In column 5 at line 7, Change "CD80αα" to --CD8αα--.

In column 5 at line 12, Change "TNFa" to --TNFα--.

In column 5 at line 12, Change "IL-1b" to --IL-1β--.

In column 5 at line 27, Change "hTNFa," to --hTNFα,--.

Signed and Sealed this
Eighth Day of March, 2016

Michelle K. Lee
*Director of the United States Patent and Trademark Office*

CERTIFICATE OF CORRECTION (continued)
U.S. Pat. No. 9,090,894 B2

In column 6 at line 45, Change "miR146a" to --miR-146a--.

In column 6 at lines 52-53 (approx.), Change "ani-miR-146." to --anti-miR-146.--.

In column 10 at line 4, Change "anti-miR146" to --anti-miR-146--.

In column 11 at line 5, Change "anti miR-146" to --anti-miR-146--.

In column 11 at line 47, Change "(Ambion.® . miRNA" to --(Ambion® miRNA--.

In column 11 at line 47, Change "page 12.)." to --page 12).--.

In column 13 at line 23, Change "anti miR-146" to --anti-miR-146--.

In column 13 at line 44, Change "down-regulated." to --downregulated.--.

In column 17 at lines 16-17 (approx.), Change "down-regulate" to --downregulate--.

In column 17 at line 25, Change "down-regulate" to --downregulate--.

In column 18 at line 66, Change "Gerline-" to --Germline- --.

In column 19 at line 13 (approx.), Change "lymphoadenopathy," to --lymphadenopathy,--.

In column 20 at line 2, Change "FACS Balibur." to --FACSCalibur.--.

In column 20 at line 39, Change "Detectin" to --Detection--.

IN THE CLAIMS

In column 28 at line 21 (approx.), In Claim 2, change "consisting of ID" to --consisting of SEQ ID--.